US008043217B1

(12) United States Patent
Rambod

(10) Patent No.: US 8,043,217 B1
(45) Date of Patent: Oct. 25, 2011

(54) METHOD AND APPARATUS TO QUANTIFY SPECIFIC MATERIAL PROPERTIES OF OBJECTS USING REAL-TIME ULTRASOUND BURST SPECTROGRAPHY TECHNIQUE

(75) Inventor: Edmond Rambod, Los Angeles, CA (US)

(73) Assignee: Bioquantetics, Inc., Los Angeles, CA (US)

( * ) Notice: Subject to any disclaimer, the term of this patent is extended or adjusted under 35 U.S.C. 154(b) by 732 days.

(21) Appl. No.: 11/827,153

(22) Filed: Jul. 10, 2007

(51) Int. Cl.
*A61B 8/00* (2006.01)
*G01H 13/00* (2006.01)
*G01H 9/00* (2006.01)
*G01N 29/00* (2006.01)

(52) U.S. Cl. ............... 600/438; 73/579; 73/628
(58) Field of Classification Search ............... 600/8
See application file for complete search history.

(56) References Cited

U.S. PATENT DOCUMENTS

| | | | | |
|---|---|---|---|---|
| 4,976,148 | A * | 12/1990 | Migliori et al. | 73/579 |
| 5,062,296 | A * | 11/1991 | Migliori | 73/579 |
| 5,115,813 | A | 5/1992 | Ylander | |
| 5,355,731 | A * | 10/1994 | Dixon et al. | 73/579 |
| 5,408,880 | A * | 4/1995 | Rhodes et al. | 73/579 |
| 5,417,215 | A | 5/1995 | Evans | |
| 5,495,763 | A * | 3/1996 | Rhodes et al. | 73/579 |
| 5,576,480 | A * | 11/1996 | Hopkins et al. | 73/38 |
| 5,685,307 | A | 11/1997 | Holland | |
| 5,746,209 | A | 5/1998 | Yost | |
| 5,903,519 | A | 5/1999 | Takahashi | |
| 5,921,928 | A | 7/1999 | Greenleaf | |
| 5,991,239 | A | 11/1999 | Greenleaf | |
| 5,997,477 | A | 12/1999 | Sehgal | |
| 6,007,489 | A | 12/1999 | Yost | |
| 6,264,609 | B1 | 7/2001 | Herrington | |
| 6,328,694 | B1 | 12/2001 | Michaeli | |
| 6,702,743 | B2 | 3/2004 | Michaeli | |
| 7,165,451 | B1 * | 1/2007 | Brooks et al. | 73/579 |
| 2001/0028371 | A1 * | 10/2001 | Su et al. | 347/19 |

OTHER PUBLICATIONS

Zadler et al, "Resonant Ultrasound Spectroscopy: theory and application." Geophys. J. Int. 2004 vol. 156, pp. 154-169.*

* cited by examiner

*Primary Examiner* — Long V. Le
*Assistant Examiner* — Angela M Hoffa
(74) *Attorney, Agent, or Firm* — Thomas I. Rozsa

(57) ABSTRACT

Real-time Ultrasound Burst Spectrography (RUBS) is a technique in which a target is stimulated using a specialized ultrasound burst signal delivered by an imaging or non-imaging ultrasound transducer and the frequency spectrum of the resulting response is analyzed and studied. The objective of this method is to interrogate (vibrate) the target and then examine its characteristic response frequency (resonance) peaks, which are unique to its mechanical and material properties (viscosity, elasticity, plasticity, visco-elasticity, etc.). The resonances could deviate from a few Hz to several KHz and the response could be in the form of a narrow peak or a band of frequencies based on the stiffness coefficient of the target material. The primary goal is to develop a reliable and non-invasive ultrasound-based diagnostic device that can be used to identify different diseases or structural abnormalities based on the stationary or dynamic target's response frequency (resonance) to a specialized acoustic excitation.

59 Claims, 19 Drawing Sheets

METHOD AND APPARATUS TO QUANTIFY SPECIFIC MATERIAL PROPERTIES OF OBJECTS USING REAL-TIME ULTRASOUND BURST SPECTROGRAPHY TECHNIQUE

BACKGROUND OF THE INVENTION

1. Field of the Invention

The present invention relates to diagnosis of medical conditions through the use of non-invasive ultrasound techniques to determine information which will assist in the clinical diagnosis of a medical condition of a patient.

2. Description of the Prior Art

In general, acoustic force generation and the use of ultrasound have been employed in the prior art to obtain information about a medical condition which can assist in a clinical diagnosis of such medical condition. The following chart sets forth the closest prior art patents which are known to the present inventor.

SUMMARY OF THE INVENTION

Real-time Ultrasound Burst Spectrography (RUBS) is a technique in which a target is stimulated using a specialized ultrasound burst signal delivered by an imaging or non-imaging ultrasound transducer and the frequency spectrum of the resulting response is analyzed and studied. The objective of this method is to interrogate (vibrate) the target and then examine its characteristic response frequency (resonance) peaks, which are unique to its mechanical and material properties (viscosity, elasticity, plasticity, visco-elasticity, etc.). The resonances could deviate from a few Hz to several KHz and the response could be in the form of a narrow peak or a band of frequencies based on the stiffness coefficient of the target material. The primary goal is to develop a reliable and non-invasive ultrasound-based diagnostic device that can be used to identify different diseases or structural abnormalities based on the stationary or dynamic target's response frequency (resonance) to a specialized acoustic excitation.

It has been discovered, according to the present invention, that there is a non-invasive method to identify the physical and structural characteristics of a portion of the human body which comprises insonifying the portion of the human body whose physical and structural characteristics are to be determined by using certain excitation schemes using diagnostic ultrasound energy so that an oscillating force is generated to set the body portion to vibrate at its resonant frequency; utilizing a specialized detector to receive the emitted response frequencies from the portion of the human body and analyze the response frequency signals to obtain an acoustic spectrum which includes the group consisting of resonant frequency, relative response amplitude, response bandwidth and response decay rate; and comparing the acoustic spectrum of the body portion obtained from the specialized detector to pre-determined known acoustic spectrum data to determine information about the physical and structural characteristics of the portion of the human body.

In addition, it has been discovered that wherein the insonification is created using real-time ultrasound burst spectrography it comprises stimulating the portion of the human body with a specialized diagnostic ultrasound burst signal and studying the frequency spectrum of the resulting response to determine unique material and structural properties of the portion of the human body from the group consisting of viscosity, elasticity, plasticity and visco-elasticity.

It has further been discovered that the present method can be used to identify different diseases based on tissue response to a specialized acoustic excitation.

It has further been discovered that the diseases that can be identified through the present invention method include static body portions from a group consisting of bones, tissue implants, mechanical implants, breast tissue, calcified tissue, sclerotic lesions, the spine and organs, and also can be used to identify dynamic body diseases identified with dynamic body conditions from the group consisting of arterial plaque, vulnerable plaque, damaged natural heart valves, malfunctioning natural heart valves, damaged mechanical heart valves, malfunctioning bioprosthetic heart valves, muscle infractions, and lungs.

It has further been discovered that the present invention can be utilized when the body part is stationary or when the body part is dynamic.

It has additionally been discovered that different excitation schemes can be utilized to achieve the results of the present invention which include delivering a chirp frequency form wherein one frequency source provides different chirps at different and predetermine frequency ranges, while the other frequency source provides a fixed frequency so that due to the difference in the applied frequencies, certain acoustic forces of certain magnitudes are generated that excite and vibrate the body portion. In addition, when a single chirp can be broken down into different segments so that the frequency scan occurs in a particular and controlled sequence so that the chirp scans cover the desired frequency scans and search for any resonance of the body portion.

It has further been discovered that the excitation frequency can be delivered through a burst sweep so that data is acquired over time wherein a fixed frequency is applied in the form of a burst and a different frequency is incremented on any subsequent trigger.

It has further been discovered that the excitation frequency can be achieved in the following sequence: the excitation signal is swept over a band of Kilohertz or Hertz range frequencies and the frequencies are modulated on a Megahertz frequency carrier; the excitation signal is obtained by mixing Megahertz frequency ultrasound signals having a delta-frequency difference which is in a Kilohertz or Hertz range; on every frequency burst, a low frequency is incremented and the duration of the excitation time is selected; two function generators each generate a burst, one function generator generating a fixed burst at the transducer Megahertz frequency while the other function generator generates another burst at the transducer Megahertz frequency plus a low frequency in Kilohertz or Hertz range; and a receiver received the frequencies emitted from the target and the received data is filtered and analyzed.

In addition, it has been discovered that the excitation frequency can be delivered as a pulse repetition frequency.

It has further been discovered that the insonification can be achieved through utilizing the following equipment: utilizing a computer with data acquisition software and two frequency acoustic generators which define and produce an excitation paradigm; signal generation, acquisition and signal processing are all automated and computer controlled; waveforms generated by signal/function generators are fed into an excitation transducer; the stimulated acoustic vibration from the body portion is detected from the group consisting of a surface microphone or a hydrophone; and the signal obtained from the detector is amplified, filtered and analyzed.

It has further been discovered that various types of transducers can be used including a single-element focused or unfocused transducer which is connected to a signal combiner; and a dual-element confocal and focused transducer which is used and each amplified signal is applied to one element of the dual-element transducer; two single-element focused or unfocused transducers can be used and each transducer is connected to a separate single function generator.

It has further been discovered that an oscilloscope can be used to visualize the inputs to the transducer and the output signal from the detector device and the excitation signal.

It has further been discovered that a mechanical or electronic imaging ultrasound transducers can be utilized with the present invention which includes a single element mechanical transducer, an imaging transducer which is a linear or a linear-array, an imaging transducer which is a phased-array electronic transducer, a non-imaging transducer which can also be selected from a group consisting of single element, multi-element, focused or unfocused.

While focusing on the utilization of the determining diseases from a body part, it is also within the spirit and scope of the present invention to provide a non-invasive method to identify the physical characteristics of a target in general which comprises: insonifying the target whose physical and structural integrity characteristics are to be determined by an excitation scheme using diagnostic ultrasound energy so that an oscillating force is generated to set the target to vibrate at its resonant frequency; utilizing a specialized detector to receive the emitted response frequency signals from the target and analyze the response frequency signals to obtain an acoustic spectrum; and comparing the acoustic spectrum of the target obtained by the specialized detector to pre-determined known resonant frequency spectrum data to determine information about the physical and structural characteristics of the target.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

In Real-Time Ultrasound Burst Spectrography ("RUBS"), the target is actively excited by a specific ultrasound energy generated and delivered by a piezoelectric crystal (transducer). The imposed energy induces a force on the target, which under certain controllable conditions, responds by vibrating at the frequency of the applied force. Maximum vibration of the target occurs only when the frequency of the applied force is very near or equal to the resonant frequency of the target. The vibration of the target produces sound that reflects the natural resonant frequency of the target. Based on the emitted resonant frequency, the typical stiffness of the target can be determined. Using this technique it may be possible to characterize and differentiate breast tissues, sclerotic lesions, vulnerable plaque, malfunctioning heart valves, muscle infract, etc. The resulting characteristics of the vibrations and resultant sound signals are different and distinguishable in different material and mediums. Thus, detection and classification of the resultant sound signals allows differentiation and diagnosis of mechanical characteristics. Also, mechanical implants can be classified based on their structural integrity which can be detected by the implant's characteristic resonant frequency once excited by a specialized scheme. An example is described in the attached presented Application # 2.

In RUBS, actuation of the target is achieved by utilizing a conventional ultrasound imaging or non-imaging transducer to project a beam of acoustic energy onto the target. By projection of the ultrasound beam on the target, an oscillating force is generated that sets the object to vibrate at its lowest natural resonant frequency. The vibrations produce sound signals at these natural or resonant frequencies, which are received by a detector. The detector can be a sensitive hydrophone, an accelerometer or a surface microphone of certain sensitivity. The detector can be located in the vicinity of the vibrating object or in some cases can be coupled with the target. The detected signals are then analyzed using the fast Fourier transform (FFT) method to identify the individual frequencies and to obtain an acoustic spectrum. The response of the target can be recorded in the form of its resonant frequency, relative resonance amplitude, bandwidth and decay rate, each contributing to the diagnosis process.

Figure 1:
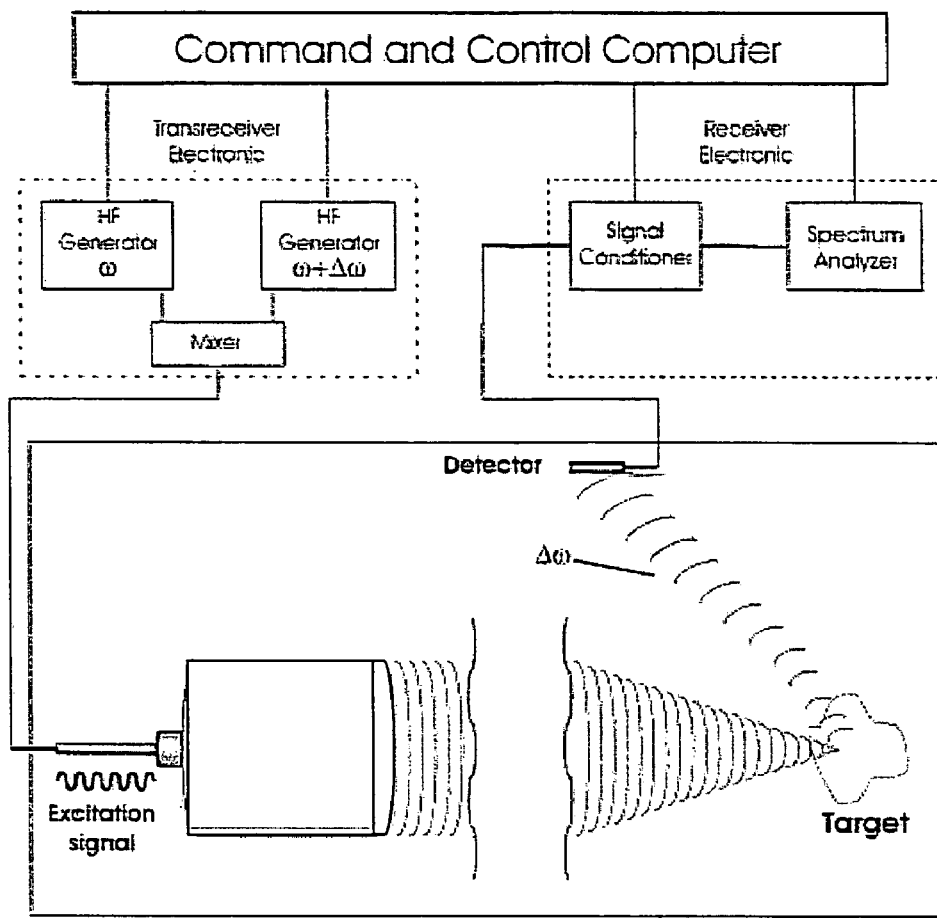
FIG. 1 is a diagram of the overall insonification procedure.

FIG. 1 shows the general setup of the insonification system. The computer along with the data-acquisition software and the two HF generators define and produce the excitation paradigm. The signal generation, acquisition and signal processing are all automated and computer controlled. Depending on the type of transducer used, the excitation waveforms may have to be modified to achieve optimum outcome. The waveforms are amplified and then input into the excitation transducer. A signal combiner is used if the transducer consists of a single-element (crystal) or only one element of a multi-element transducer. For example, when dual-element transducers are used, the mixer is eliminated and each amplified signal is applied to one element of the transducer. This will be discussed in detail later in the next sections. Some of the transducers are custom-made in order to achieve the acoustic signal mixing. The piezoelectric transducers used in RUBS are either focused or flat (unfocused), either single element or dual element confocal (focused only). The transducers are cylindrical and vary in crystal diameter starting at ½ inch.

An accelerometer, a surface microphone, a hydrophone or scanning laser vibrometer may be used to detect the stimulated acoustic radiation from the target. The accelerometer is a general purpose vibration detector with very high sensitivity at low frequencies. The surface microphone is used for non-invasive applications and has a very high receiving sensitivity. The hydrophone is used for semi-invasive applications and is a wide range, general purpose detector with a very high receiving sensitivity. The signal obtained from each one of these detectors is then amplified, filtered and analyzed. A laser vibrometer may be used in preliminary stages to confirm the results obtained by the hydrophone, microphone and accelerometer. Oscilloscopes are used to visualize the inputs to the transducer, as well as the output signal from the detection device and the excitation pulse.

Depending on the condition of the target, whether it is stationary or in motion, the excitation process may vary in nature. In the stationary case, the excitation energy can be easily focused on the target. Artificial implants (bone, spinal, etc.) are good examples of such conditions. In dynamic cases, the excitation must be timed on an external trigger since the target is in motion and the excitation pulse must act at some specific time intervals during the cycle where the noise floor is non-existent or minimal. Cases related to the cardiovascular or pulmonary systems qualify in such categories of targets. In such cases, factors such as breathing, heart beat, heart valve closure, flow noise, etc. could be key parameters in determining the timing for excitation since they produce sound artifacts which reduce the sensitivity of the system. The excitation energy is delivered in a pulsed form rather than in a continuous form so that the transducer will not contribute to the detected acoustic radiation. In such dynamic conditions, the Chirp Excitation paradigm is used.

1.0 Chirp Excitation Scheme

In the chirp frequency excitation scheme, one high frequency function generator chirps while the other provides a fixed frequency. Due to the difference in the applied frequencies, certain forces are generated that can excite/vibrate the target.

The excitation is generally applied when there is little or no noise due to the dynamic behavior of the target. Therefore, the excitation as well as analysis processes occur in a very short and timed window which is generated based on a trigger. For cardiovascular applications, the trigger can be the "R" wave of the QRS complex of an ECG signal or other available sound signals (i.e., specific heart sound) given that the sound intensity is adequate. The detection device is given a 'window' of time just after the excitation to acquire the emanating acoustic signals and avoid undesired background noise. It is very important to have a trigger so that the excitation process is appropriately timed.

In this case, chirps are generated after every trigger. If the environment is not noisy then the single chirp can be broken down into different segments so that the frequency scan occurs in a particular and controlled sequence. This sequence is called one presentation. This is done to maximize the time for which each frequency span is introduced which in return, increases the signal-to-noise ratio (SNR). These chirps scan the desired frequency spans and search for any resonance emanating from the target. The chirp width can be set before applying the excitation. This technique is fast in the sense that the results are obtained right at the end of the trigger. Hence, this is the most preferred method of excitation. A complete description of this technique with detailed diagrams and schematics can be seen in the presented Inventions Application # 3.

2.0 Burst-Sweep Excitation Scheme

Figure 2:
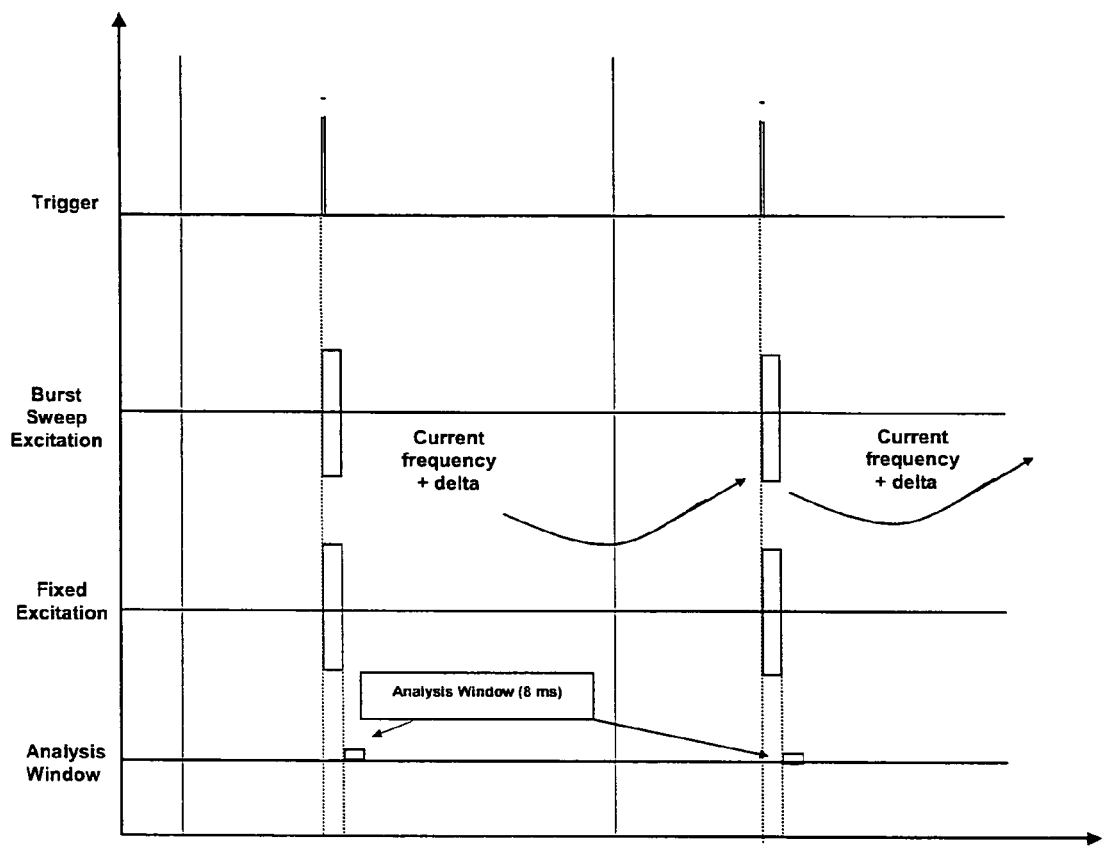
FIG. 2 is a diagram of the burst-Sweep excitation scheme.

In the burst sweep scheme, data is acquired over a long period of time, (refer to FIG. 2). This might take several minutes and can use multiple triggers and thus is suitable for cases where the target is stationary. Again depending on the transducer used, the signals might be individually applied or mixed using a combiner. On every trigger, fixed frequencies are applied in the form of a burst, but the difference frequency ($\Delta f$) is incremented on every subsequent trigger. Hence this method is called burst sweep as the response sweeps from a certain start to stop frequency. The burst width can be selected before the excitation is applied. Even though the SNR of the response is relatively high when burst sweep is applied, the chirp paradigm is often preferred since it is faster.

During the first step of a static target interrogation, burst sweep excitation is applied and a first-hand estimate of the response frequency is obtained. Once the approximate target resonance frequencies are available, then the trial is carried out with the chirp excitation paradigm. For example, the burst sweep excitation involves the following steps:

1) In burst sweep technique, the excitation is swept over a band of Hertz (Hz) or kilohertz (KHz) range frequencies, but this frequency band is modulated on a high frequency (MHz) carrier.
2) The low frequencies are obtained by mixing two Megahertz signals, which are slightly different in frequency (for example: for a 3 MHz transducer, a 5 KHz frequency can be obtained by mixing 3 MHz+5 KHz and a 3 MHz signals).
3) Direct mixing of the signals can be done before the transducer by using a device called the combiner. This is done when a single element (crystal) transducer is used. When a dual-element transducer is used, mixing is done externally in the medium.
4) On every trigger, the low frequency is incremented (by a frequency step designated as delta). The sequence is controlled by a program written in LabVIEW.
5) The duration of the excitation pulse is user selectable and can be anywhere from 1 msec to 24 msec. Generally, a 10 msec pulse width is adequate for use.
6) The timing diagram for this scheme is shown in FIG. 2.
7) Both function generators are set to generate a burst. One of them generates a fixed burst at the transducer resonant frequency while the other generates the transducer frequency plus the low frequency (Hz or KHz). The entire excitation sequence is controlled by a program written in LabVIEW, via a GPIB bus.
8) The receiver section consists of a hydrophone, surface microphone, laser vibrometer or an accelerometer.

9) Two types of windows are used for data filtering. The forced window is open for a short period of time during the analysis time typically for 8 msec. An exponential window is also used which gives a sharp response.

3.0 Pulse Repetition Frequency Scheme

Pulse repetition frequency technique (PRF) is a technique which is in the form of burst just like the burst sweep methodology. A detailed description of this technique is presented in the presented Invention Application # 4. The PRF technique is not generally used since it is time consuming like the burst sweep. The concept is similar to burst sweep except the burst is in a different format.

As described earlier, different types of transducers can be used for generating the acoustic energy. These can be categorized into two families: 1) Imaging transducers and 2) non-imaging transducers. The imaging transducers can be single element, linear array or phased-array (i.e., cardiac or abdominal). The non-imaging transducers can be either single or multiple element and either focused or unfocused (flat). All the types of transducers work with the chirp and burst sweep excitation schemes. However, depending on the transducer used, the setup of the power amplifiers needs to be altered. The following section describes the primary schemes by which the transducer is used to generate the excitation.

4.0 Transducers Configuration Schemes 4.1 Dual Element Transducers

Figure 3:
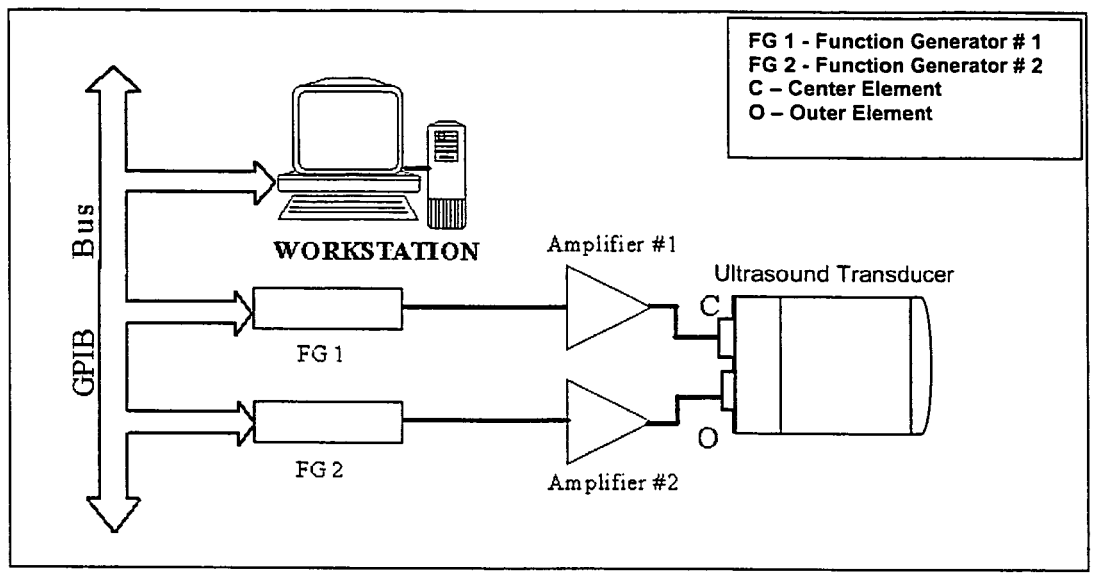
FIG. 3 is an excitation scheme for a dual-element confocal transducer.

For a dual element transducer, the signal generated by the two function generators is applied to individual amplifiers as seen in FIG. 3. The outputs of the amplifiers are connected to the center and outer element of the dual element transducer. The monitoring system controls the function generators that generate the burst sweep or chirp excitation via the GPIB bus.

4.2 Dual Element Transducers with Signal Combining

Figure 4:
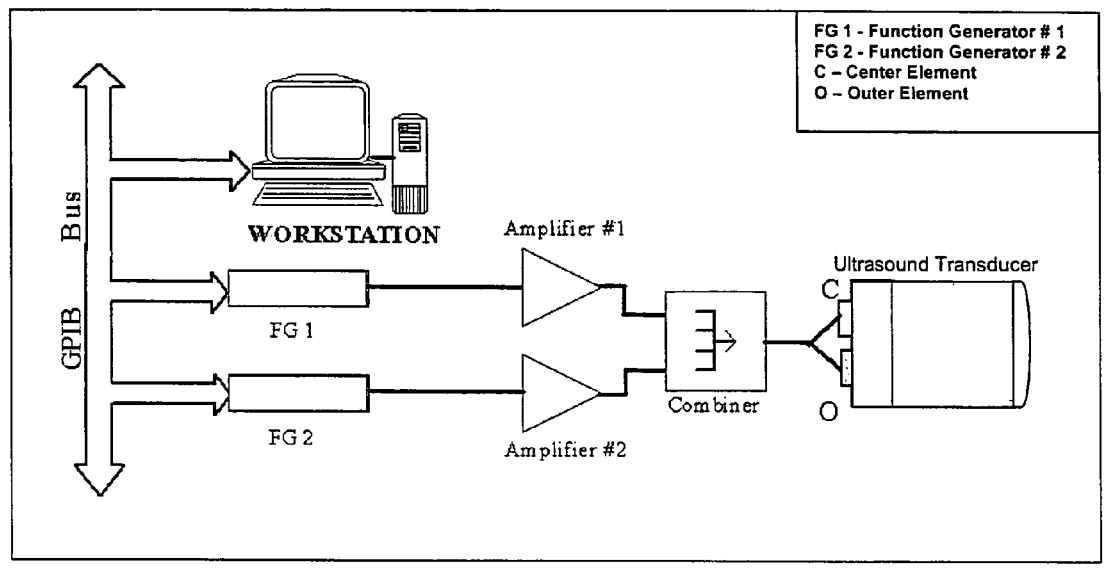
FIG. 4 is a signal combining excitation scheme for a dual-element confocal transducer.

In this mode, the outputs from the amplifiers are connected together to yield a combining effect or an amplitude-modulated wave with 100% modulation index as illustrated in FIG. 4. The monitoring system via GPIB bus, sets function generator FG#1 and function generator FG#2 to generate burst fixed, burst sweep and chirp excitation schemes.

4.3 Single Element Transducer with Signal Combining

Figure 5:
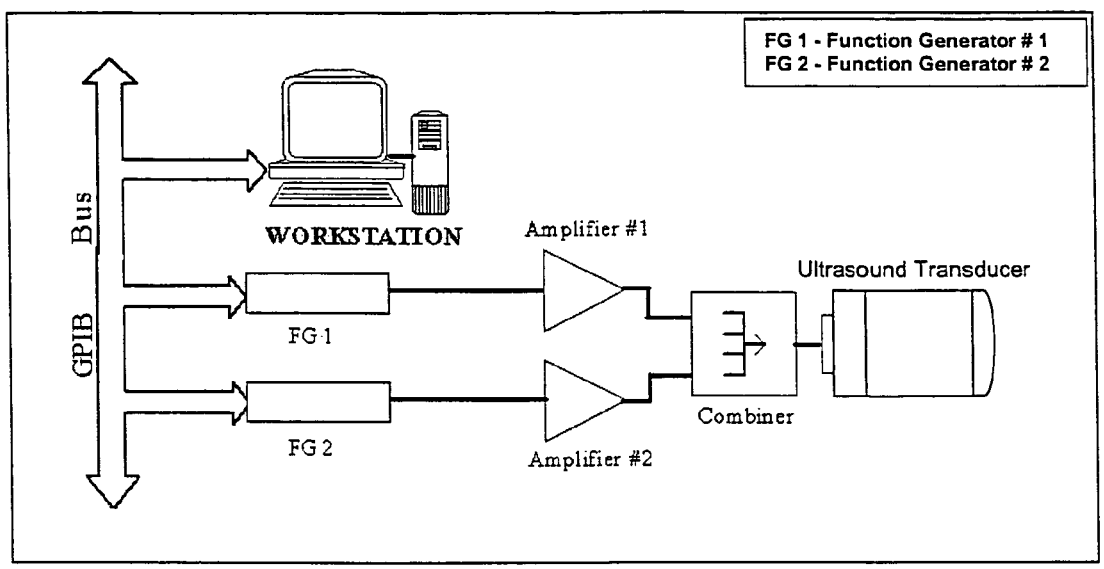
FIG. 5 is a signal combining excitation scheme for a single-element transducer.

A single element transducer works only with a signal combining technique as illustrated in FIG. 5, as it does not have the second element that can generate the difference frequency. The monitoring system via GPIB bus, sets function generator FG#1 and function generator FG#2 to generate burst fixed, burst sweep and chirp excitation schemes.

In sections 4.2 and 4.3 above which involve signal combining, the signal can be directly generated by amplitude modulating the low frequency signal on the carrier frequency externally. This eliminates the need for a combiner and also for a high frequency amplifier. This technique has been described in the attached presented Invention Application # 2, Section 3.

5.0 Potential Applications 5.1 Brachytherapy: Active acoustic method is explored for detecting and imaging brachytherapy metal seeds.

[1] Improving the use of vibro-acoustography for brachytherapy metal seed imaging: a feasibility study.

Brachytherapy seeds detection using vibro-acoustography.

5.2 Contrast agent micro-bubbles: Vibro-acoustography of contrast micro-bubbles in degassed water produced quantitative flow measurements from analysis of their acoustic emission.

[3] Vibro-acoustography: quantification of flow with highly-localized low-frequency acoustic force.

5.3 Micro-calcification of valves and arteries: The method can detect micro-calcification within breasts, and promises to provide high quality images of calcification within arteries.

[4] Detection of Calcium Deposits on Heart Valve Leaflets by Vibro-acoustography.

[5] Imaging of vulnerable plaque in coronary artery by parametric ivus and acoustic microscopy.

[6] Non-invasive elasticity imaging in small vessels: experiments on tissue-mimicking phantoms.

5.4 Plantar Fascia: Detect changes in the plantar fascia which causes pain in the heel.

[7] Resonance Frequency of the Plantar Fascia.

5.5 Achilles tendon: Estimate the mechanical property of the Achilles tendon in vivo via resonant frequency using clinical ultrasound and an accelerometer system.

[8] Mechanical Property of the Achilles Tendon in vivo.

5.6 Ablated Tissue: To visualize thermally ablated tissue. Lesions caused due to HIFU.

[9] Progress in the elastographic imaging of radiofrequency ablated thermal lesions.

5.7 Osteoporosis

[10] Low-frequency ultrasonic velocity measurements in human calcaneal trabecular bone.

5.8 Cancer detection

[11] Sonoelastic detection of cancer in radical prostatectomy specimens.

5.9 Bone Assessment: Assessment of bone structure.

[12] A dual-frequency method for ultrasound assessment of bones: Model study.

5.10 Monitoring of surgery using low frequency ultrasound

[13] Ultrasound Surgery Monitoring using Vibroacoustogvaphy.

6.0 Invention Applications

INVENTION APPLICATION # 1

RUBS Application to Tuning Forks for Proof of Concept

Introduction

The goal of this investigation was to develop a standard for testing the ultrasound transducers and prove the concept of RUBS.

TABLE 1

Tuning forks physical dimensions
(resonant frequencies are defined in air)

| Resonant Frequency (Hz) | Width (mm) | Total Length (mm) | Thickness (mm) |
| --- | --- | --- | --- |
| 3000 | 25.2 | 106.6 | 4.80 |
| 4995 | 24.5 | 94.0 | 4.75 |
| 5000 | 25.2 | 94.5 | 4.80 |
| 8000 | 25.0 | 83.3 | 4.80 |

Description of Experimental Investigation

Figure 6:
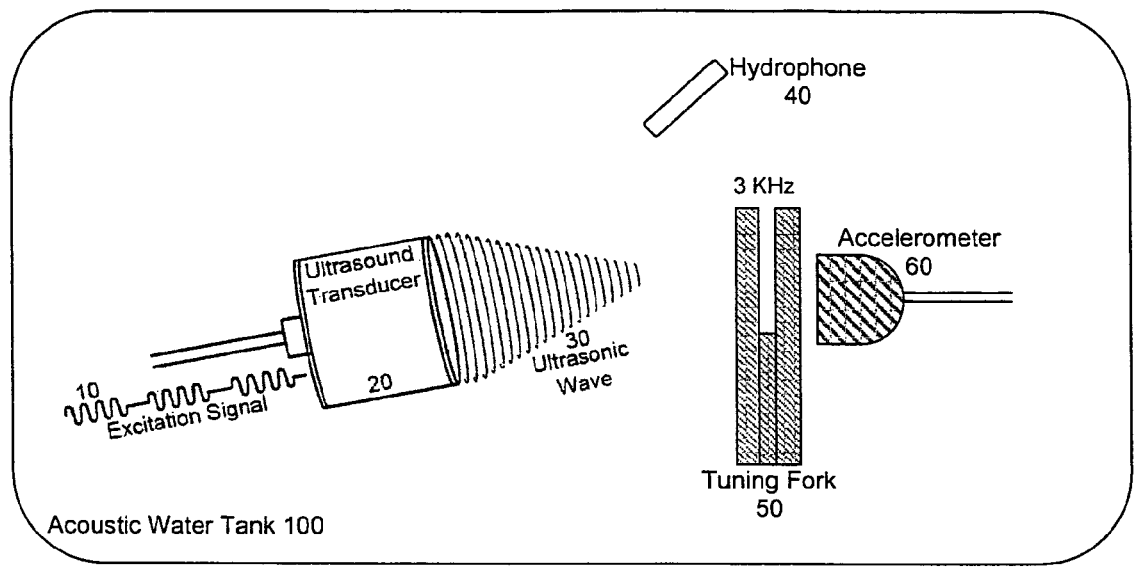
FIG. 6 is an image of the experimental setup with a 3-KHz tuning fork (not touching)

For evaluating the resonant frequency of a tuning fork, a 1" diameter, spherical-focused transducer with a 4.0 MHz carrier frequency was used. A tuning fork was placed near or touching the accelerometer in a water tank. It was observed that the exact position of the tuning fork relative to the accelerometer did not change the detected resonant frequency. The resulting resonance of the fork was detected by the accelerometer and by a hydrophone for comparison. Three position of the tuning fork relative to the accelerometer were used:

1. Not Touching—The tuning fork was placed near (<2 mm) the accelerometer but not touching (shown in FIG. 6).

Figure 7:
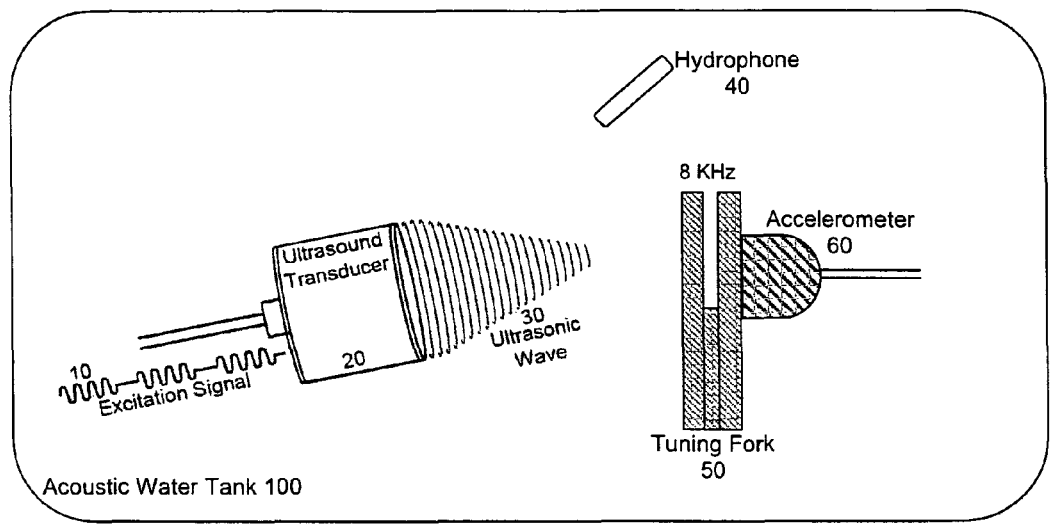
FIG. 7 is an image of the experimental setup with a 8-KHz tuning fork touching the accelerometer when the transducer is placed in an angle.
Figure 8:
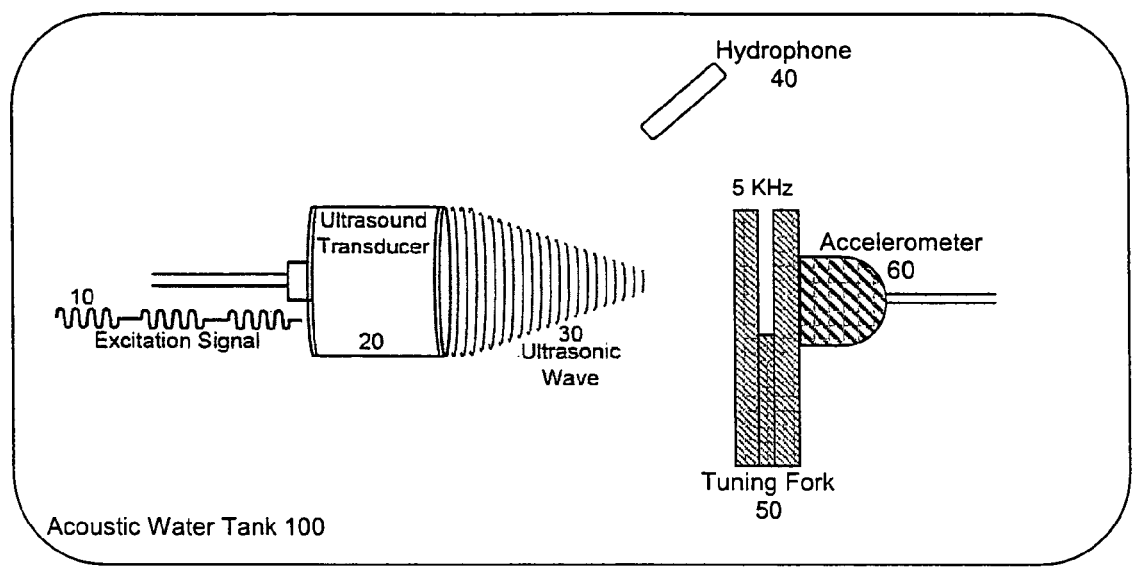
FIG. 8 is an image of the experimental setup with a 5-KHz tuning fork touching the accelerometer when the transducer is placed with no angle.

2. Touching Angle—The base of the tuning fork was held against the accelerometer and the transducer was kept in the holder and angled to insonify the tip of the tuning fork (shown in FIG. 7).
3. Touching direct—The base of the tuning fork was held against the accelerometer and the transducer was held by hand so that it was perpendicular to the tuning fork (shown in FIG. 8).

When the fork was placed in water the resonant frequency will decrease by around 10% but the actual value depends on the exact geometry of the tuning fork which was unknown in this case. We selected the 3, 5 and 8 KHz forks in the study. Table 2 gives the measured values found for each fork in the water tank. It was found that the 'not touching' case produced the cleanest results.

TABLE 2

Resonant frequencies in air and water.

| Resonant Frequency in Air (Hz) | Resonant Frequency in Water (Hz) | Percentage Decrease (%) |
|---|---|---|
| 3000 | 2672 | 10.93 |
| 5000 | 4464 | 10.72 |
| 8000 | 7168 | 10.40 |

Invention Application # 2

RUBS Application to Bjork-Shiley Convexo-Concave (BSCC) Heart Valves to Determine Their Acoustic Signatures in Order to Classify Their Structural Integrity Introduction The state of the BSCC heart valves, whether intact or with single-leg-separation (SLS) can be identified by the acoustic signature of their outlet struts. This acoustic imprint is the resonant frequency of the strut and is different for each valve depending on the physical dimensions of the intact strut and integrity of the fractured ones. A typical range for the resonant frequency of an intact BSCC valve would range from 6.9 KHz to 7.8 KHz. The broken BSCC valves can be classified into two categories:

1) Broken and completely separated
2) Cracked but touching (kissing contact)

The fractured strut when completely separated resonates at around 2 KHz, while the fractured strut with touching ends vibrates at its maximum between 3.7 KHz to 4.4 KHz. Since the strut resonance occurs at low KHz frequencies, it is not feasible to vibrate the strut directly with low KHz frequencies. Hence, ultrasound MHz frequencies are used as carriers to deliver the low KHz frequencies to the strut. The carrier is modulated with the low frequency and sent toward the strut through a medium that is suitable for the propagation of ultrasound waves. Water is the most preferred medium in vitro for medical ultrasound since it is inexpensive and also the characteristics of sound in water are similar to that in blood. However, the water needs to be degassed to prevent formation of small bubbles due to cavitation. Once the strut is excited, the response is acquired by a hydrophone, surface microphone, laser vibrometer or an accelerometer. The acquired signal is then processed using various windowing and filtering techniques. The quality of the acquired signal depends on factors like the type of transducer (flat or focused), method of excitation, choice of receiver, filtering and other processing techniques. The present invention uses several approaches to excite the strut. These techniques have been described below.

Section 1: Burst Sweep Scheme

Figure 9:
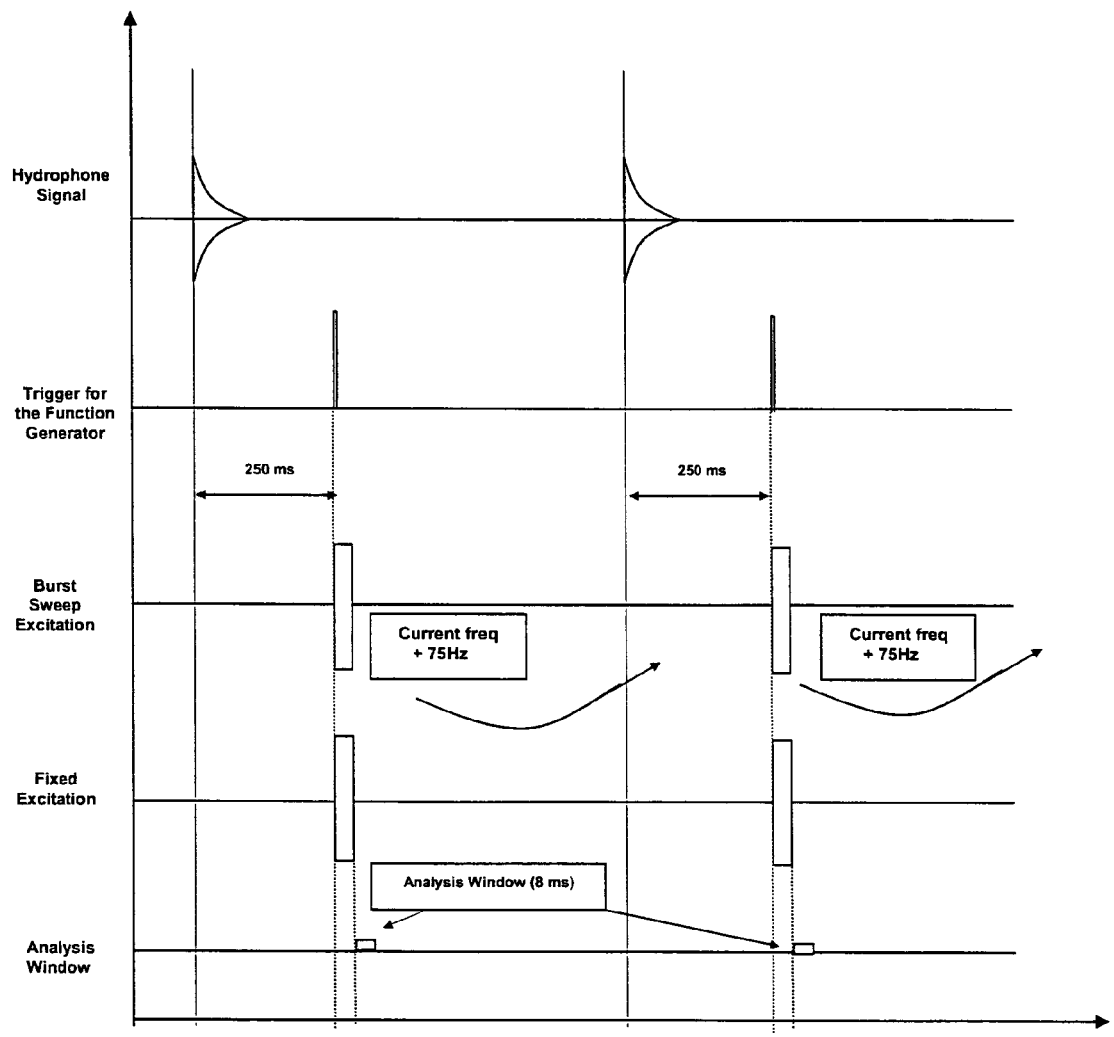
FIG. 9 is a timing diagram for the burst-sweep scheme.

1) In burst sweep technique, the excitation is swept from 1 KHz to 10 KHz.
2) The low frequencies can be obtained by mixing two MHz signals, which are slightly different in frequency (for example: for a 3 MHz transducer, a 5 KHz frequency can be obtained by mixing 3 MHz+5 KHz and 3 MHz).
3) Mixing can be done before the transducer by directly mixing a signal using a combiner. This is done when a single element transducer is used. When a dual element transducer is used, mixing is done externally in the medium.
4) The trigger for the system is set at 1 Hz and on every trigger the low frequency is incremented by 75 Hz. The sequence is controlled by a program written in Lab-VIEW. Hence, to cover a spectrum of 9 KHz, with increments of 75 Hz, it takes 120 sec to complete the entire acquisition (see FIG. 9)
5) The duration of the excitation is user selectable and can be varied from 1 msec to 15 msec. Generally, a 10 msec pulse width is used.
6) The timing diagram for this scheme is shown in FIG. 9.
7) When a dual element transducer is used, the two Megahertz frequencies are connected to the two elements of the transducers. In this setup, the mixing occurs externally in the medium where the sound waves from the two elements intersect.
8) When a single element transducer is used, the two frequencies are mixed by a combiner.
9) Both the function generators are set to generate bursts. One of them generates a fixed burst at the transducer resonance frequency while the other generates the transducer frequency plus the low frequency. The entire excitation sequence is controlled by a program written in LabVIEW, via a GPIB bus.
10) The receiver section consists of either a hydrophone or an accelerometer.
11) Two types of windows are used for data filtering. The forced window is open for a short period of time during the analysis time typically for 8 msec. An exponential window is also used which gives a sharp response.

Section 2: Chirp Excitation Scheme

Figure 10:
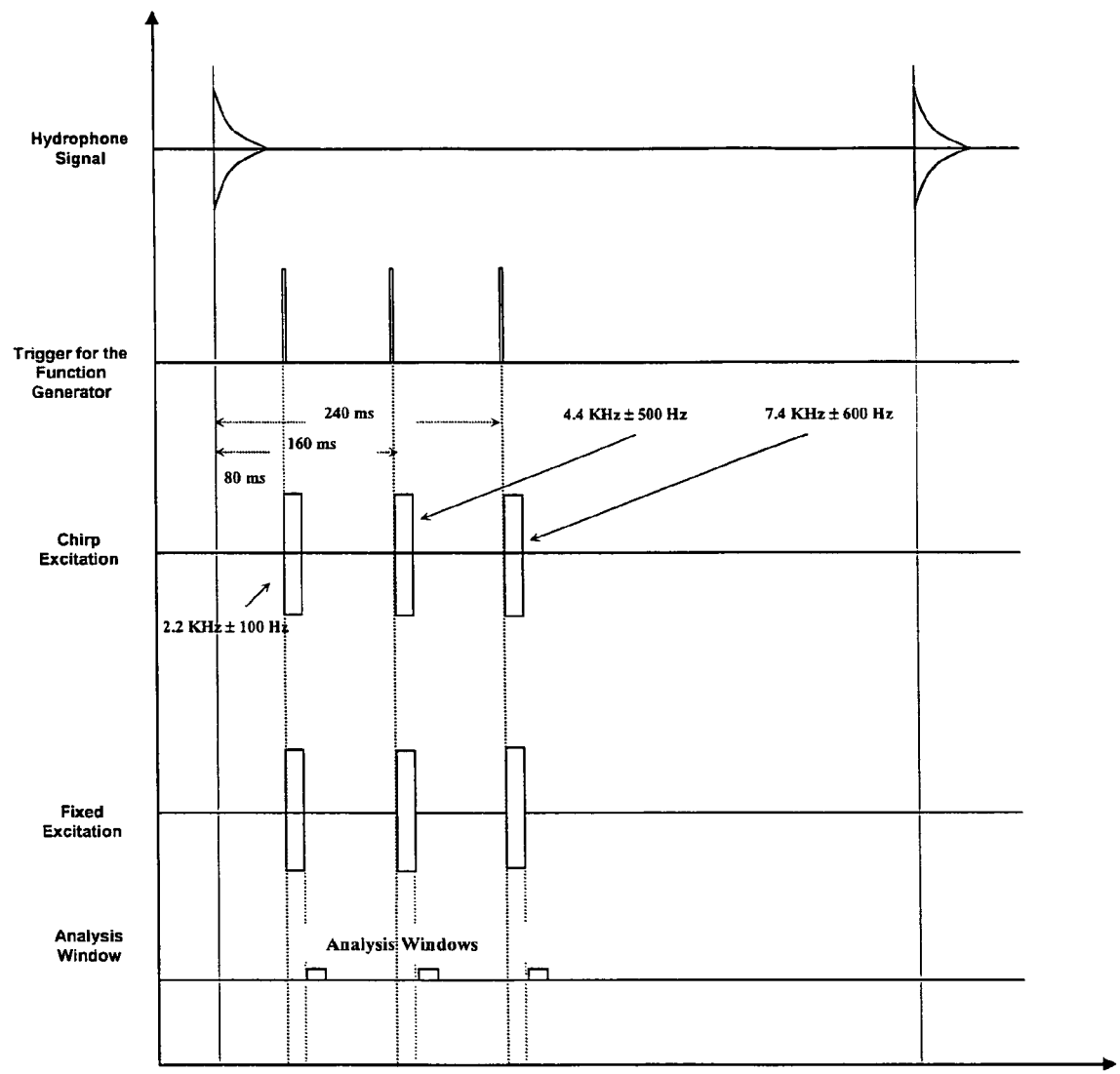
FIG. 10 is a time diagram for the chirp excitation scheme.

1) In this particular method of excitation, three chirps are generated after every trigger. This sequence is called one presentation and investigates the presence of 2-KHz-SLS, 4-KHz-SLS and 7-KHz-Intact resonances (FIG. 10).
2) The chirp width can be set before application of the excitation and can range from 1 to 15 msec. Typically, a width of 3-8 msec is preferable.
3) The first chirp is programmed at 80 msec after the trigger, and has a center frequency of 2.2 KHz and bandwidth of 200 Hz. The second chirp occurs at 160 msec and has a center frequency of 4.4 KHz and bandwidth of 1000 Hz. The third and the final chirp is presented at 240 msec post valvular closure and has a center frequency of 7.4 KHz with a bandwidth of 1200 Hz.
4) Refer to FIG. 10 for the timing characteristics of this scheme.
5) In chirp frequency excitation, function generator FG#1 is chirping while function generator FG#2 provides a fixed frequency. Due to the difference in the applied frequencies, we can generate low (KHz) frequency excitation that can excite the strut.
6) One generator generates a fixed frequency, which is the transducer resonance frequency while the other generator generates the transducer frequency plus the sweep.

7) In the chirp excitation scheme, both dual-element and single-element transducers can be used.
8) For a dual-element transducer, the two frequencies are connected to the two elements of the transducer and for a single element transducer a combiner is used.
9) The combining schemes for burst sweep and chirp are similar.

Section 3: Amplitude Modulation Scheme

Figure 11:
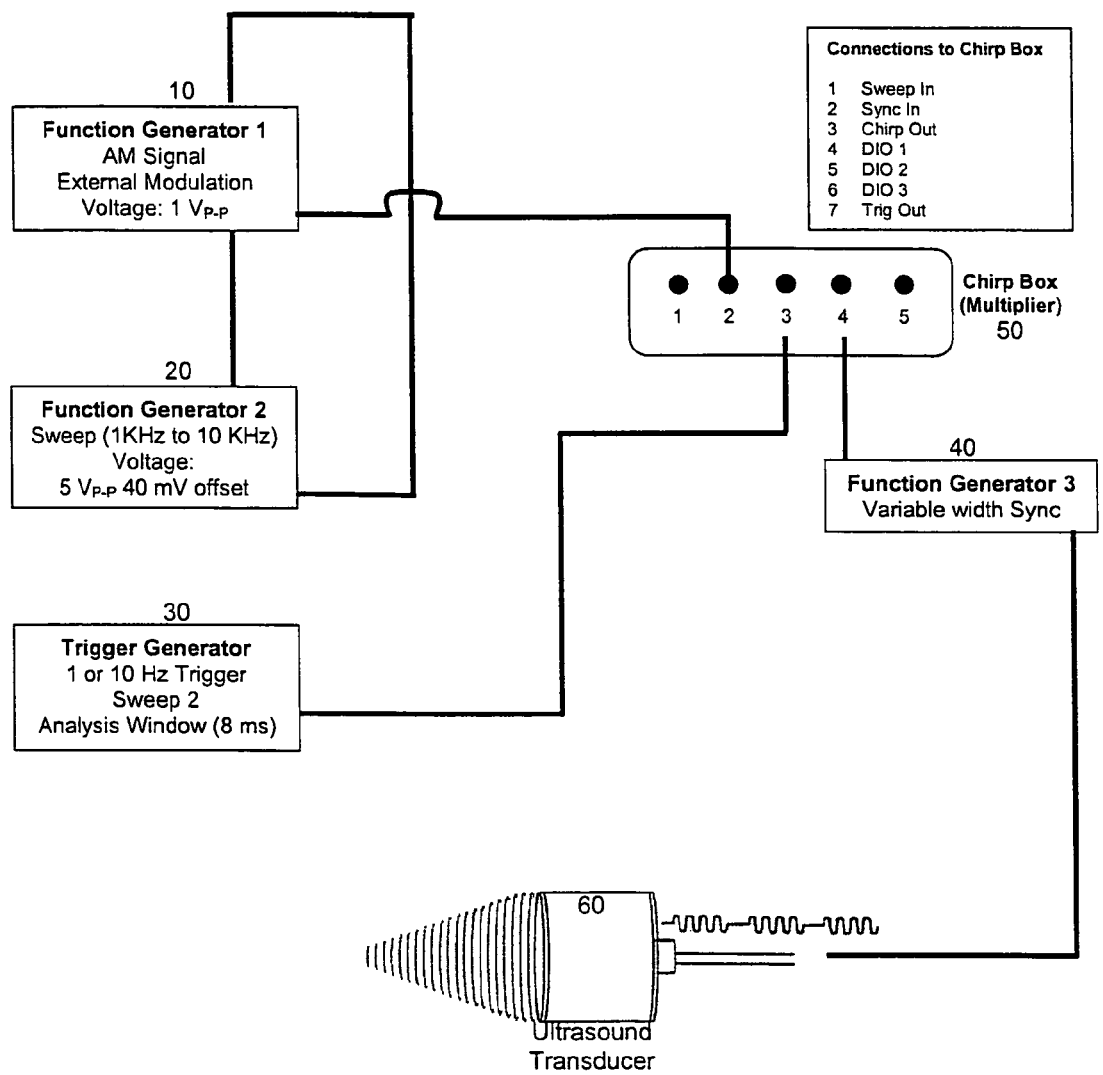
FIG. 11 is a setup for burst amplitude modulation.

1) In this technique the low (KHz) frequency signal is amplitude modulated on the carrier (MHz) frequency. The carrier frequency is the transducer resonant frequency. The requirement for this is that the modulation needs to be 100%.
2) This technique requires using a multiplier, which simply multiplies two inputs. See FIG. 11 for the setup diagram. The chirp box is such a circuit that can multiply two inputs. Also another circuit is made using AD835AN, a 4-quadrant multiplier that serves the same purpose.
3) Function generator FG#1 and function generator FG#2 together generate the amplitude-modulated waveform. Function generator FG#1 is set to output an amplitude modulation (AM) waveform with carrier signal set to 1 $V_{p-p}$ and frequency equal to the carrier frequency. The modulating signal is inserted to function generator function generator FG#1 externally by FG#2 function generator.
4) Function generator FG#2 generates a sweep from 1 KHz to 10 KHz with amplitude of 5 $V_{p-p}$ with a DC offset of 40 mV. This serves as an input to function generator FG#1.
5) Function generator FG#1 outputs a continuous amplitude-modulated waveform. This is connected to one of the inputs of the multiplier.
6) Function generator FG#3 is set to generate a burst with burst width set between 1 msec to 15 msec. Usually, a burst width of 10 msec is used. The trigger for the burst is set to 60 beats per minute (bpm). The frequency is set to the transducer excitation frequency. The sync of this function generator FG#3 is used as one to the inputs to the multiplier.
7) The output of function generator FG#1 is multiplied by the sync of function generator FG#3 and provides a burst amplitude-modulated waveform.
8) The output of the multiplier is connected to the power amplifier and the output of power amplifier is inserted to the transducer.
9) The receiver section for this technique remains the same.

Invention Application # 3

Complete Description of Chirp Scheme for BSCC Heart Valve Classification

Basic Concept of the Chirp Scheme

Figure 12:
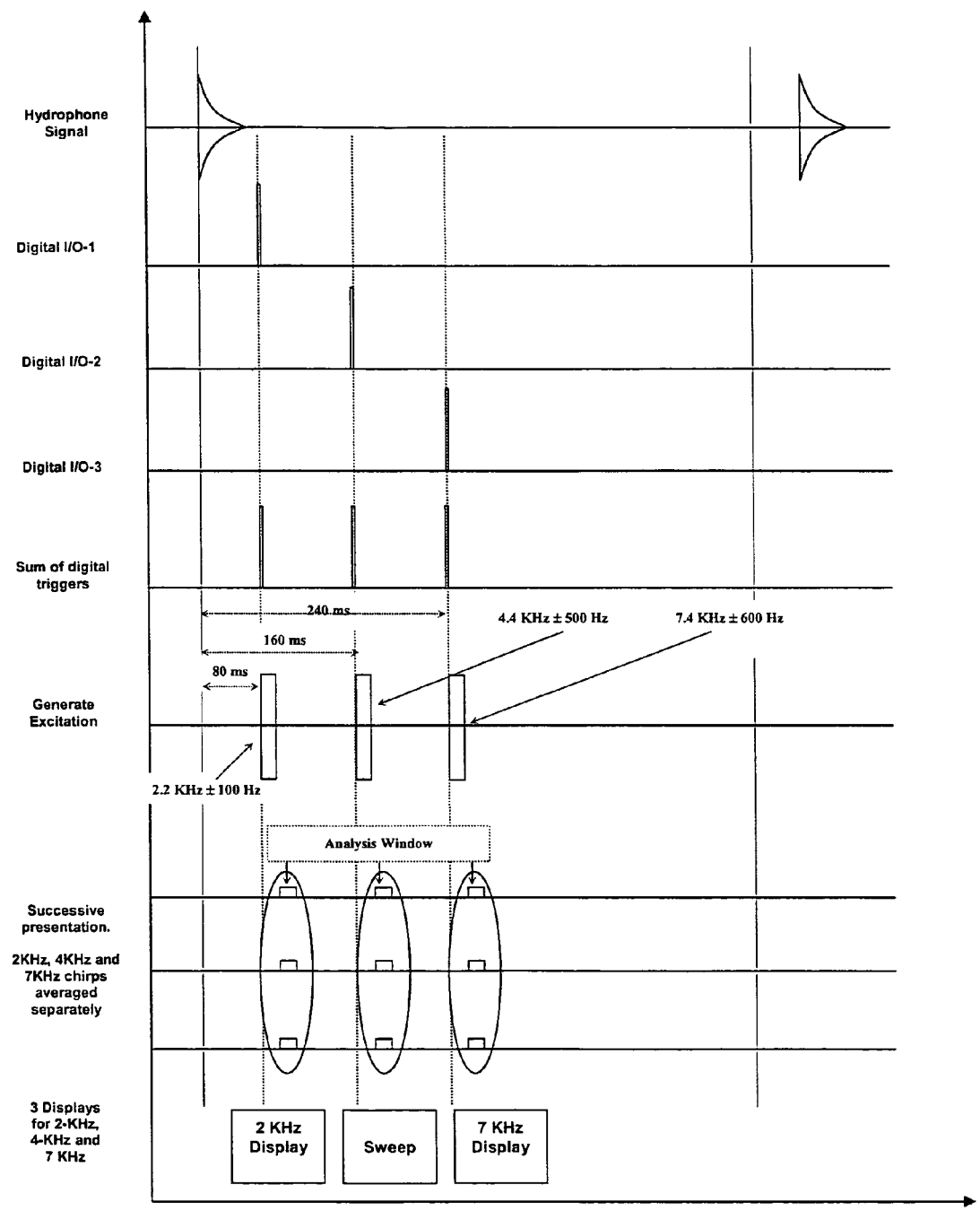
FIG. 12 is a depiction of the fundamentals of the chirp excitation scheme.

1. In this method of excitation, three chirps are generated after every closure of the valve to search for the resonant frequency of the valve. This sequence is called one presentation. The following example will further manifest the chirp excitation scheme.
2. The first chirp is programmed to occur after an initial delay of 80 ms following the main trigger, and has a center frequency of 2.2 KHz and bandwidth of 200 Hz. The initial delay can be changed by a knob in the LabView program. The second chirp occurs at 160 ms and has a center frequency of 4.4 KHz and a bandwidth of 1000 Hz. The third and the final chirp is presented at 240 ms post-impact and has a center frequency of 7.4 KHz with a bandwidth of 1200 Hz. The center frequencies and spans can be changed programmatically.
3. The time duration between the first and the second chirp and between the second and the third chirp is approximately 80 ms due to the speed of the function generator to change states (i.e., refresh memory, etc.).
4. The chirp width can be set before application of the excitation (Range: 1-15 ms). Therefore, it is advised to select a suitable width because a larger width can result in reduction of the amplitude and a small width can fail to excite the strut completely. Typically, a width of 3-8 ms is used.
5. The analysis window occurs at the end of each chirp.
6. The DAQ box (controlled by LabView program) generates digital pulse at varying times, on three separate digital I/O lines. These are used by the signal analyzer as trigger to separately average the spectrum obtained in each chirp.
7. The three digital triggers are then added in the chirp box to give the final trigger that causes the occurrence of the three chirps.
8. A six channel Pulse analyzer is used to do the analysis. The first chirps of successive presentations are averaged separately than the second and the third. This allows us to view three different displays.
9. The analyzer is set to exponential averaging. The acquisition window is 62 ms long, with an exponential window of 31 ms. The resolution is set to 16 Hz and the span is 12.8 KHz
10. Refer to FIG. 12 for the timing considerations of the chirp excitation scheme.

DETAILED DESCRIPTION OF THE METHOD

Figure 13:
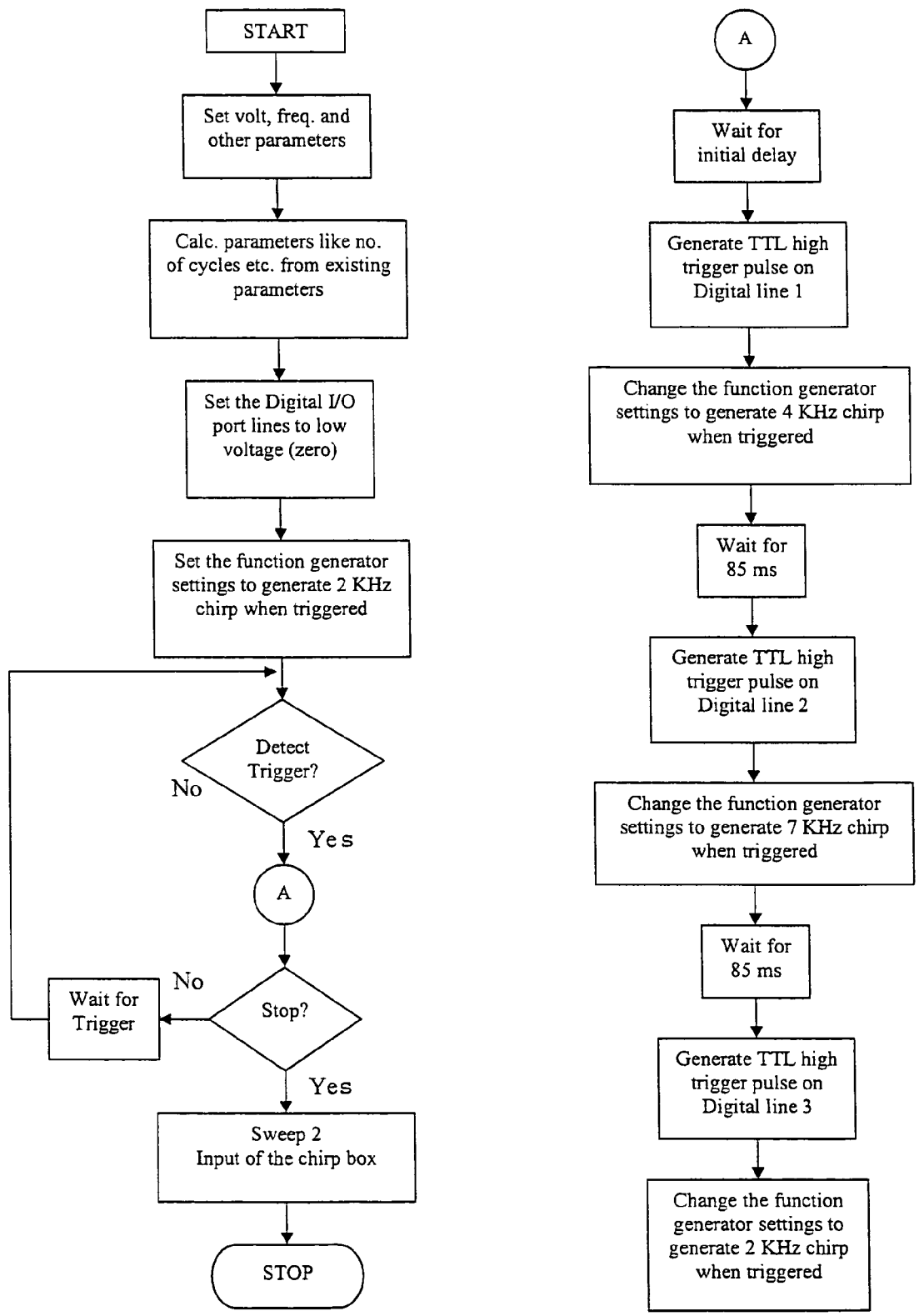
FIG. 13 is a flowchart of the program for the chirp excitation scheme.

The flowchart for the program is shown in FIG. 13. The flow of program steps is similar for both chirp schemes. The only difference would be the setup and the commands sent to the function generators to generate different functions. Other than that the basic concept of the chirp scheme remains the same for both the types of chirp excitation.

1) In the first step, the user feeds in the values for input voltage, pulse width, frequency of transducers, etc.
2) Then the parameters, like number of cycles, frequency spans and other parameters needed to set the function generators are calculated.
3) Set the digital output port to zero.
4) Set the function generator to generate the first chirp signal. The function generators are set in external trigger mode. So they will not generate any activity until they receive the trigger. The external trigger mode setting remains on for the entire duration of the program. So, even though the function generators are set to chirp they will not do it unless they receive a trigger.
5) Now the function generators are in ready state and waiting for the trigger.
6) In BSCC case we use valve closure as our main trigger. When the program detects impact, it enters the loop.
7) It waits for the user specified initial delay and then generates a pulse on digital line 1. This pulse is connected to the external trigger input of the function generators, through the adder circuitry.
8) When the first pulse on line 1 reaches the function generators, the first chirp is generated.
9) Now the software changes the settings of the function generator to generate the second chirp.

10) The program waits for 85 ms and then generates a pulse on the digital line 2. This acts as a trigger to the function generators, which in turn generate the second chirp on this trigger.
11) The program changes the setting of the generators to generate third chirp.
12) It waits for 85 ms and then generates a pulse on digital line 3. This acts as a trigger to the function generators, which in turn generate the third chirp on this trigger.
13) The program changes the setting of the generators to generate the entire sequence again. It sets the system to generate the first chirp and then the entire loop from step 5 is repeated, till the user presses the stop button.
14) Once the stop button is pressed, the function generators are set to a very low voltage and all GPIB instruments are set to local mode.

The flow of program is similar in AM chirp and the chirp excitation scheme with two function generators. The only difference would be the command set and the set up which has been explained in the next section.

Three Chirps with Two Separate Outputs

The following section describes the setup for generating three chirps with two separate function generators.

Figure 14:
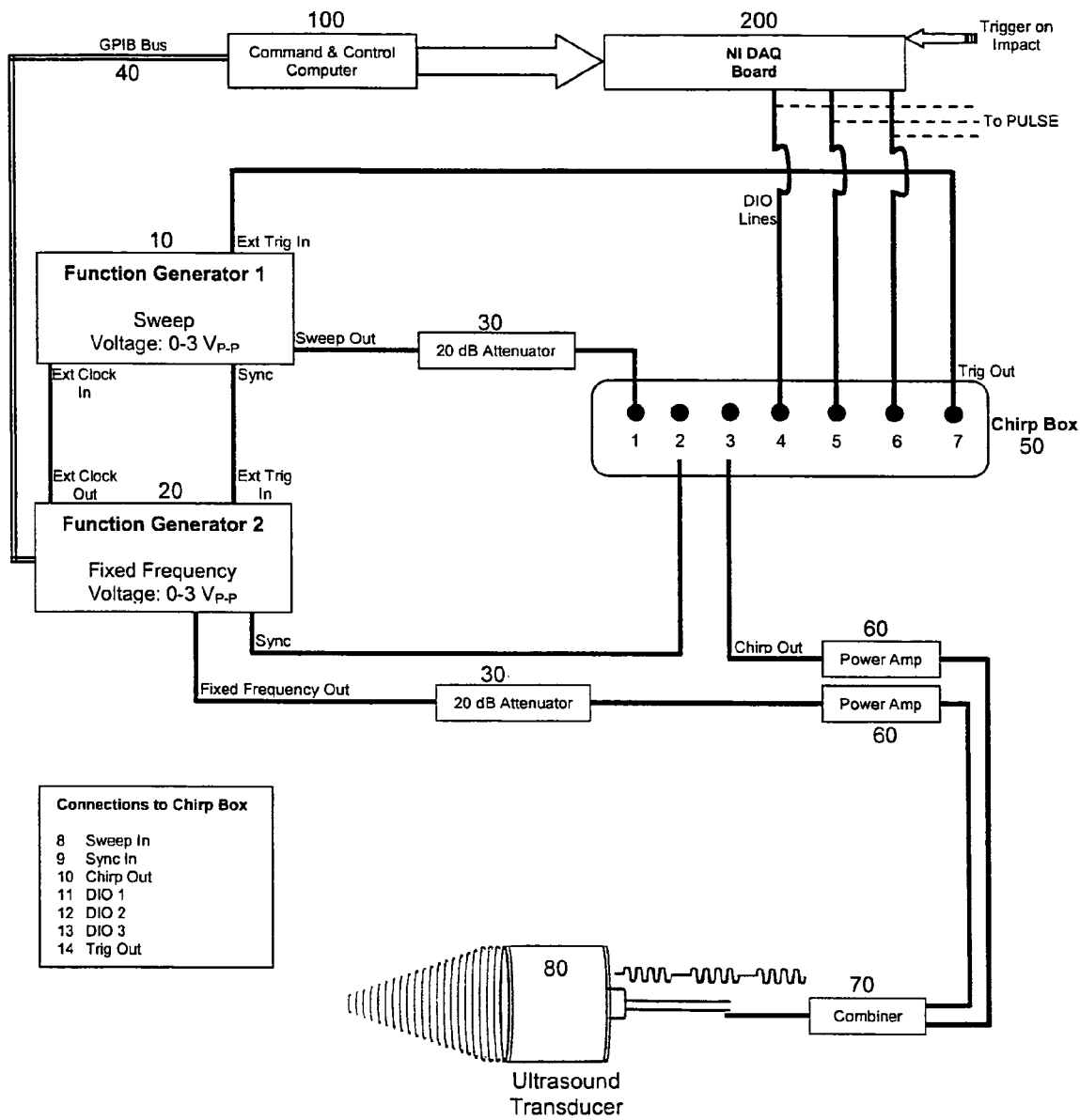
FIG. 14 is picture showing the setup for generating three chirps with two function generators.
Figure 15:
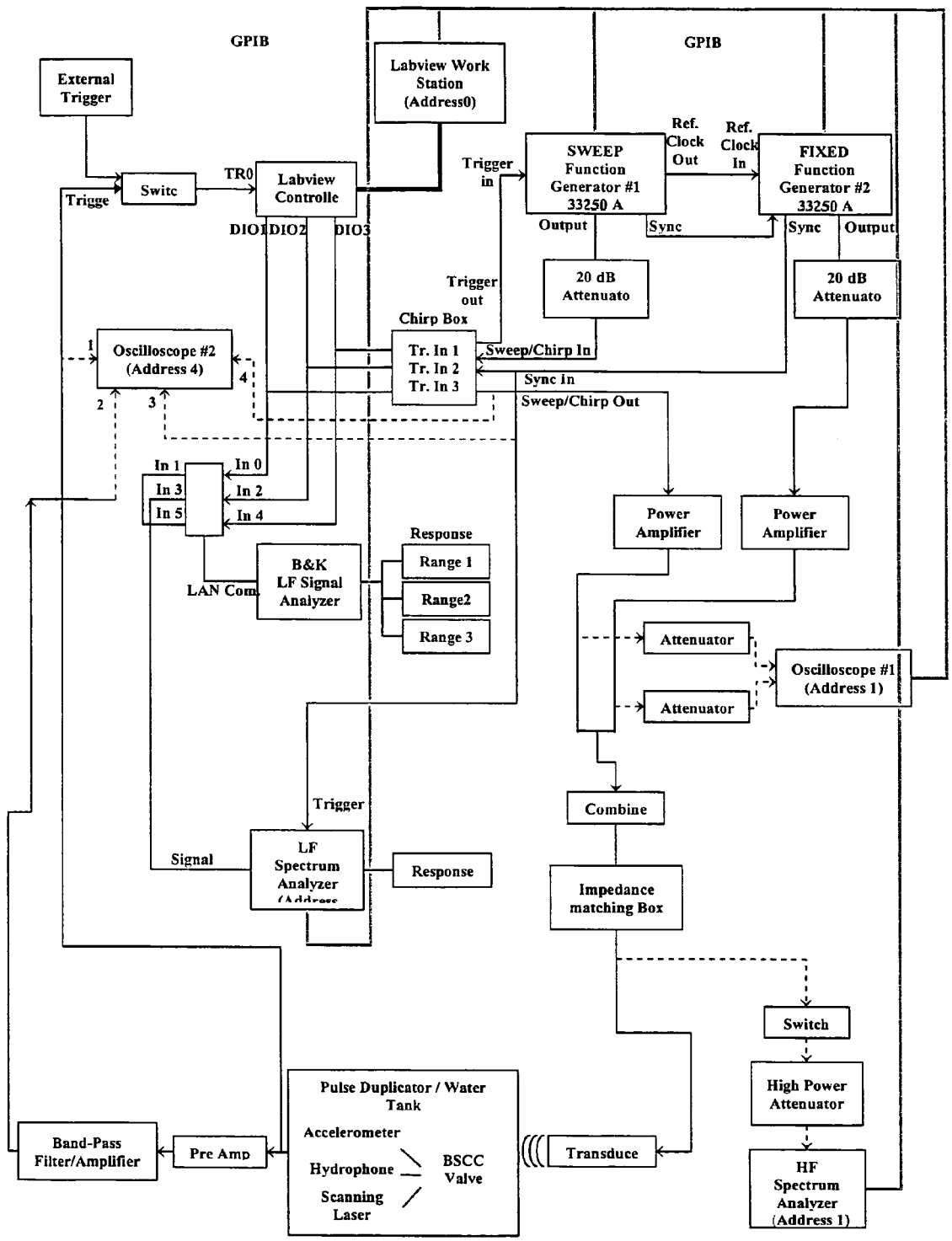
FIG. 15 is a complete schematic of the procedure for generating three chirps with two function generators.
Figure 16:
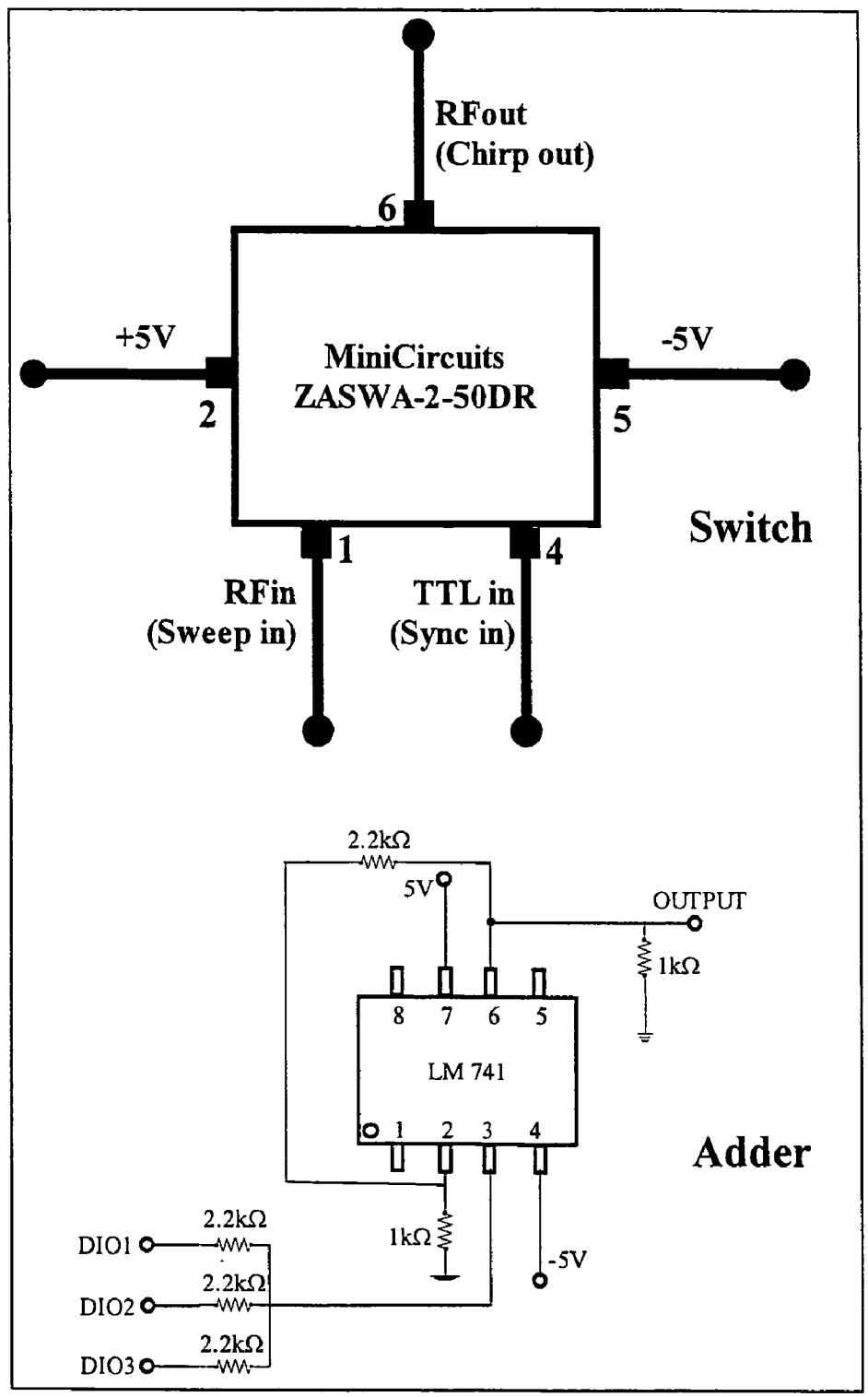
FIG. 16 is a schematic of the chirp box.

1. In this procedure, (refer to FIG. 14) function generator FG#1 works as a sweep generator and the other one (function generator FG#2) works as a fixed frequency generator. The clocks of the two function generators are matched in order to achieve synchronization.
2. The two function generators are controlled via GPIB bus by a LabView program.
3. Three digital I/O lines from the NI DAQ board are connected to the DIO 1, DIO 2 and DIO 3 of the chirp box which form the inputs to an adder circuit. The output of the adder is "Trig out" which acts as the trigger for generating the three chirps. This "Trig out" is connected to the "Ext Trig" in of the Sweep function generator FG#1.
4. These I/O lines are also connected to the inputs of Pulse signal analyzer.
5. The sync from function generator FG#1 is connected to the "Ext Trig" in of the fixed frequency generator FG#2.
6. The sync of function generator FG#2 is connected to sync in terminal of the chirp box. This acts as the TTL signal for the high-speed "GaAs" switch.
7. The output of function generator FG#1 is connected to the Sweep in terminal of the chirp box. This serves as the RF input to the switch.
8. The Chirp out terminal of the chirp box is connected to the power amplifier. The other end of the power amplifier goes to one of the inputs of the combiner.
9. The output of function generator FG#2 is directly connected to the second power amplifier. The output is connected to the second input of the combiner.
10. The output of the combiner is connected to the transducer.
11. A complete schematic of this method including the receiver section has been shown in FIG. 15.
12. The chirp box consists of two circuits. One of them is the adder circuit which is used to add the pulses generated on the digital I/O lines. The output of the adder is used to trigger the function generators. Refer to FIG. 16 for the schematic.
13. The second circuit is the high-speed GaAs switch. It is a small device that is fixed inside of the chirp box. The need for the switch arose because the sweep function generator returned to its original frequency after the sweep was complete. This would give us continuous voltage that was harmful to the transducer.
14. Basically the switch has two inputs, the RF in and the TTL in. The sweep from function generator FG#1 is connected directly to the RF in and the sync from function generator FG#2 is connected to the TTL in.
15. The switch is on when the TTL signal is high and is off when it is TTL low. Function generator FG#2 generates a TTL high sync pulse whenever the excitation is present.
16. Thus, the continuous signal generated by function generator FG#1 is gated by the sync signal and only the chirp or sweep signal is separated out.

Description of the Three Amplitude Modulation Chirps

The following section describes the setup for generating three amplitude modulated chirps with three separate function generators.

Figure 17:
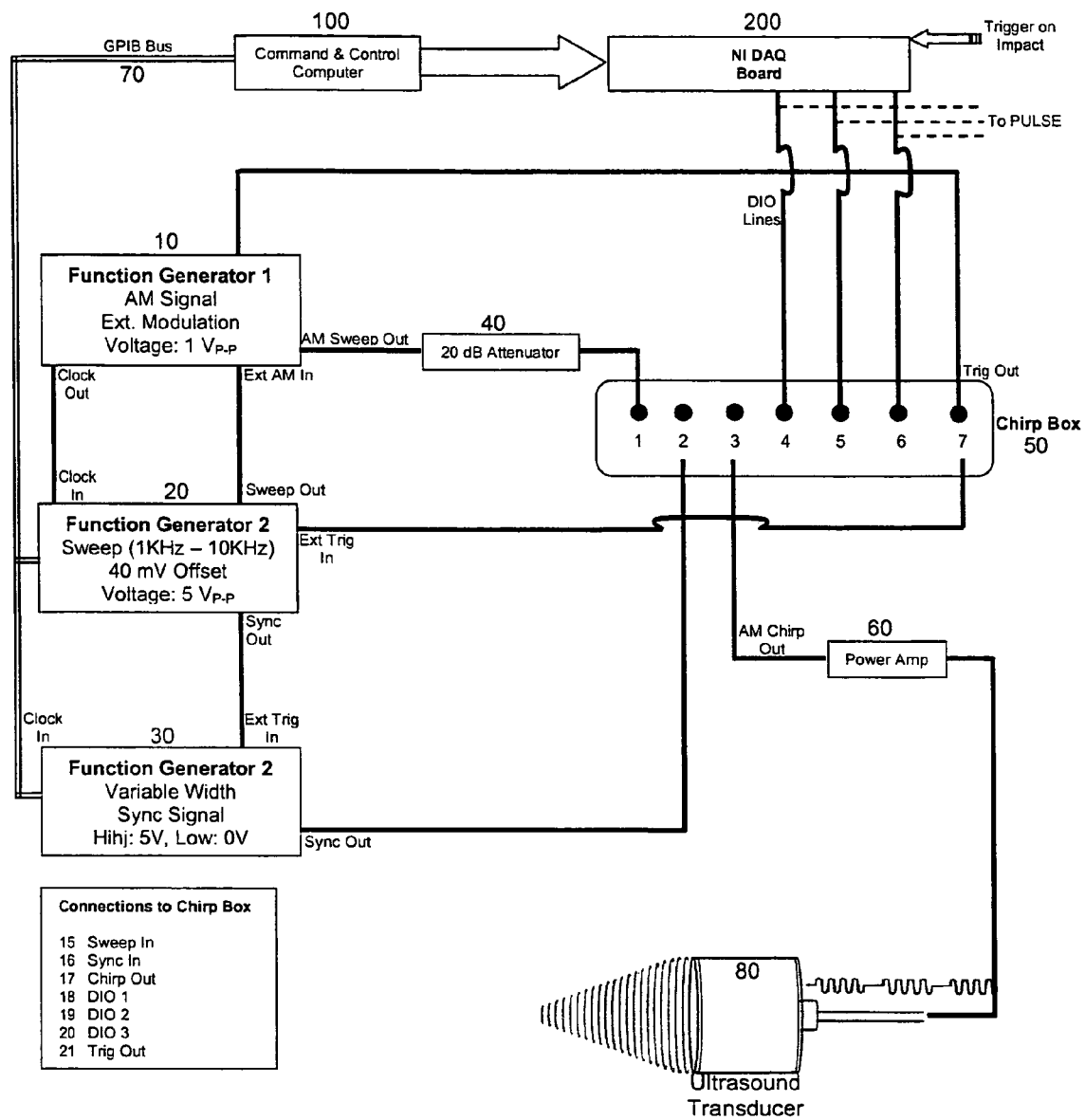
FIG. 17 is a setup for generating three Amplitude Modulated chirps with three function generators.
Figure 18:
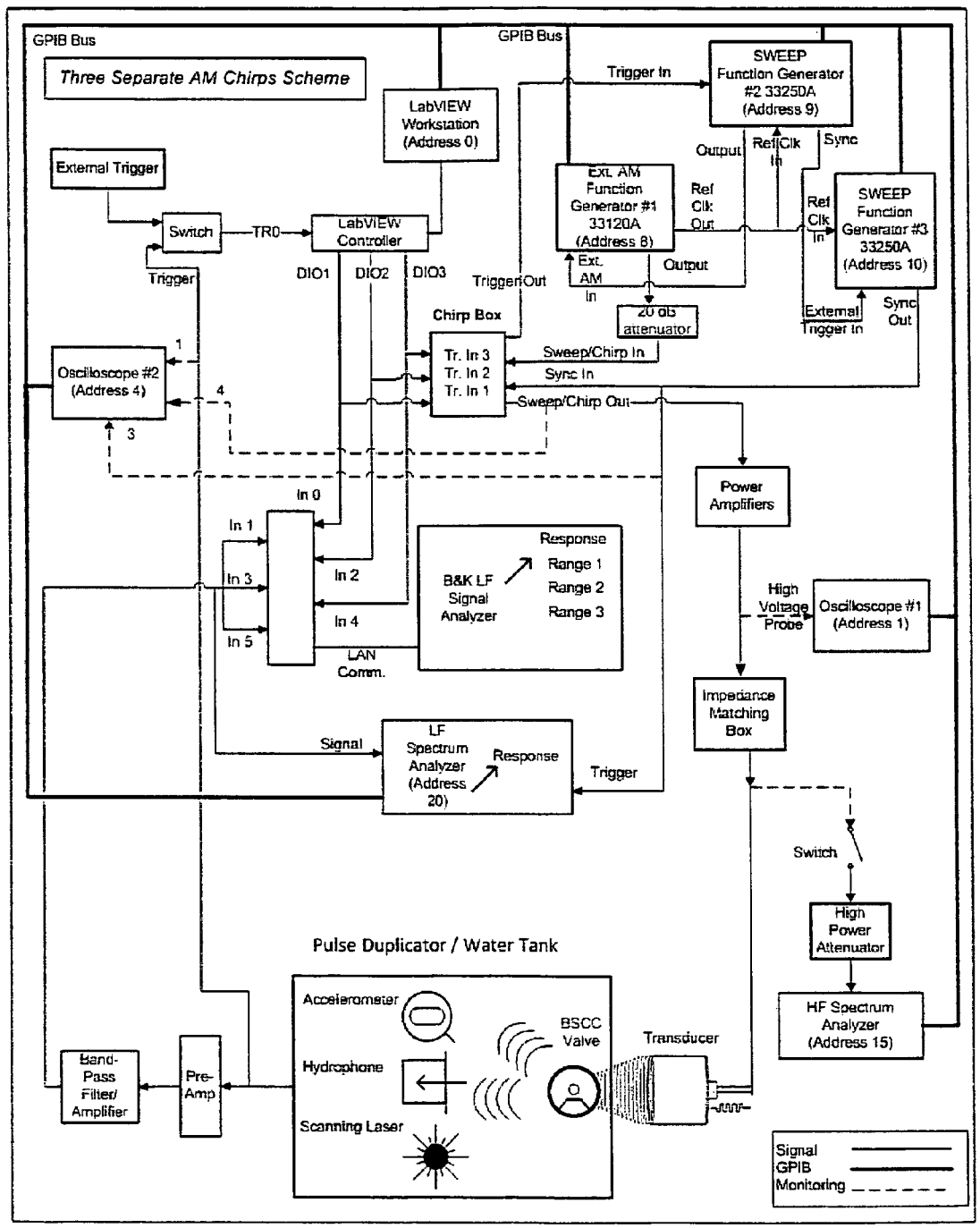
FIG. 18 is a complete schematic of the procedure for generating three AM chirps with three function generators.

1. In this procedure, (refer to FIG. 17) three function generators are used. Function generator FG#3 is merely used as a variable width pulse generator. Function generator FG#2 works as a sweep generator and the other one works as an amplitude modulator. The clocks of the three function generators are matched in order to achieve synchronization.
2. All the function generators are controlled via GPIB bus by a LabView program.
3. Three digital I/O lines from the NI DAQ board are connected to DIO 1, DIO 2 and DIO 3 of the chirp box which form the inputs to an adder circuit. The output of the adder is Trig out which acts as the trigger for generating the three chirps. This Trig out is connected to the Ext Trig in of the Sweep function generator FG#2.
4. These I/O lines are also connected to the inputs of Pulse signal analyzer.
5. The sync from function generator FG#2 is connected to the Ext Trig in of the variable width pulse generator FG#3.
6. The sync of function generator FG#3 is connected to sync in terminal of the chirp box. This acts as the TTL signal for the high-speed GaAs switch.
7. The output of function generator FG#1 is connected to the Sweep in terminal of the chirp box. This serves as RF input to the switch.
8. The Chirp out terminal of the chirp box is connected to the power amplifier. In this case, a fixed frequency signal is not required because the excitation signal is already amplitude modulated.
9. The output of the power amplifier is connected to the transducer.
10. A complete schematic of this method including the receiver section has been shown in FIG. 18.

Invention Application # 4

Pulse Repetition Frequency (PRF) Paradigm

The application of this idea is fundamentally the same as our previous schemes. The primary difference is that the KHz-range acoustic pressure is created from MHz-range impulses rather than through a difference frequency or waveform modulation.

It is necessary to note the resonant frequency of the target when selecting a fixed pulse repetition frequency. If the resonant frequency is not known then the pulse repetition rate must be swept to probe for the maximum response.

Figure 19:
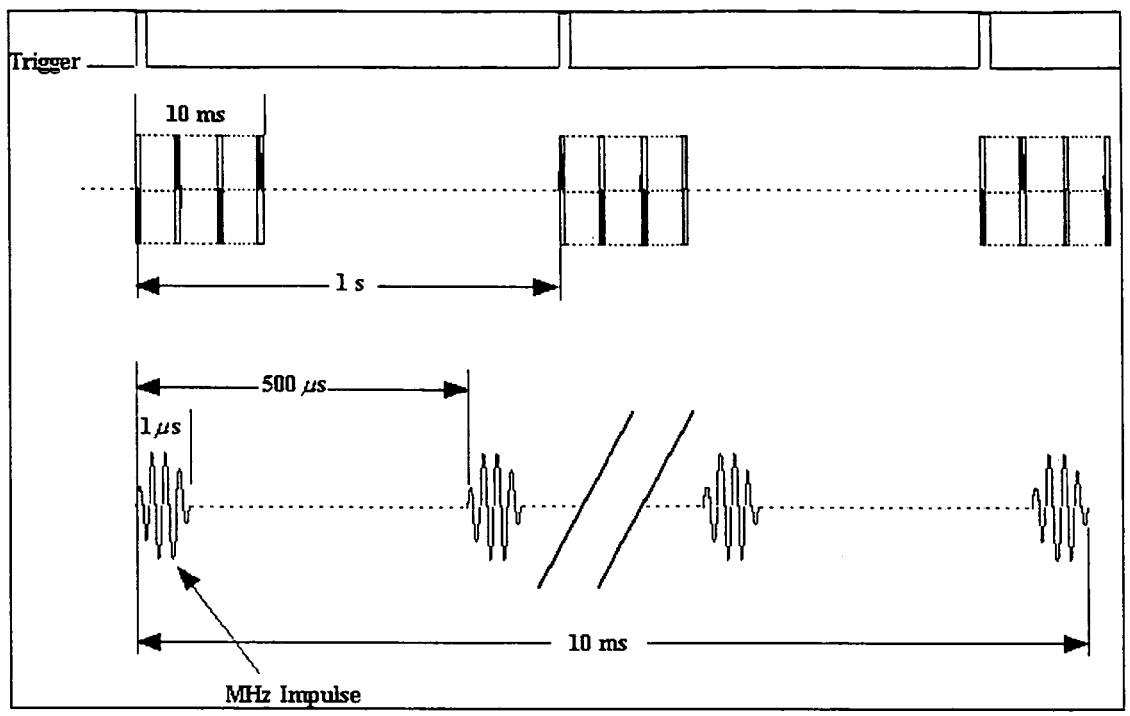
FIG. 19 is an example for the application of the PRF scheme for a 2-KHz target.

FIG. 19 illustrates an example for application of the PRF for a 2-KHz target:

The 500 μs spacing corresponds to a 2-KHz target and will vary inversely with the target resonant frequency. The value of 1 μs for the impulse length is the approximate lower limit. The duty cycle can be increased up to 50%. For the case above the impulse would then be 250 μs long, which is exactly half the duration of one cycle of the resonant frequency.

The pulse repetition method requires less power than continuous bursts that are amplitude modulated or combined to produce a difference frequency. The amplitude of the high-frequency impulses can therefore be higher than that of a continuous wave. An analogy would be that during the 10 ms burst we are striking with a periodic hammer rather than pushing back and forth continuously.

Defined in detail, the present invention is a non-invasive method to identify the physical and structural characteristics of a portion of a human body, comprising: (a) insonifying the portion of the human body whose physical and structural characteristics are to be determined by using certain excitation schemes using diagnostic ultrasound energy so that an oscillating force is generated to set the body portion to vibrate at its resonant frequency; (b) utilizing a specialized detector to receive the emitted response frequencies from the portion of the human body and analyze the response frequency signals to obtain an acoustic spectrum which includes the group consisting of resonant frequency, relative response amplitude, response bandwidth and response decay rate; and (c) comparing the acoustic spectrum of the body portion obtained from the specialized detector to pre-determined known acoustic spectrum data to determine information about the physical and structural characteristics of the portion of the human body.

Defined more broadly, the present invention is a non-invasive method to identify the physical characteristics of a target, comprising: (a) insonifying the target whose physical and structural integrity characteristics are to be determined by an excitation scheme using diagnostic ultrasound energy so that an oscillating force is generated to set the target to vibrate at its resonant frequency; (b) utilizing a specialized detector to receive the emitted response frequency signals from the target and analyze the response frequency signals to obtain an acoustic spectrum; and (c) comparing the acoustic spectrum of the target obtained by the specialized detector to pre-determined known resonant frequency spectrum data to determine information about the physical and structural characteristics of the target.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A non-invasive method to identify physical and structural characteristics of a portion of a human body, comprising:
   a. setting a time of origin in a time scheme of the non-invasive method;
   b. generating a first pulse from a trigger at a first point in time of the time scheme, which first pulse is sent to simultaneously trigger first and second function generators, the first function generator transmitting a first fixed frequency having a defined time width to an ultrasonic transducer, the second function generator transmitting a first chirp of modulated frequencies having the defined time width to the ultrasonic transducer wherein the modulated frequencies are created from modulating a fixed frequency equivalent to the first fixed frequency and swept frequencies having a first center frequency with a first bandwidth, the ultrasonic transducer generating an acoustic energy to impact and excite the portion of the human body, using at least one detector to detect a signal of response frequencies from the portion of the human body excited by the acoustic energy and analyzing the detected signal at the end of the defined time width;
   c. generating a second pulse from the trigger which is sent to simultaneously trigger the first and second function generators at a second point in time of the time scheme, the first function generator transmitting a second fixed frequency having a defined time width to the ultrasonic transducer, the second function generator transmitting a second chirp of modulated frequencies having the defined time width to the ultrasonic transducer wherein the modulated frequencies are created from modulating a fixed frequency equivalent to the second fixed frequency and swept frequencies having a second center frequency with a second bandwidth and the defined time width, the ultrasonic transducer generating an acoustic energy to impact and excite the portion of the human body, using at least one detector to detect a signal of response frequencies from the portion of the human body excited by the acoustic energy and analyzing the detected signal at the end of the defined time width;
   d. generating a third pulse from the trigger which is sent to simultaneously trigger the first and second function generators at a third point in time of the time scheme, wherein the first function generator transmits a third fixed frequency having the defined time width to the ultrasonic transducer, the second function generator transmits a third chirp of modulated frequencies having the defined time width to the ultrasonic transducer wherein the modulated frequencies are created from modulating a fixed frequency equivalent to the third frequency and swept frequencies having a third center frequency with a third bandwidth and the defined time width, the ultrasonic transducer generating an acoustic energy to impact and excite the portion of the human body, using at least one detector to detect a signal of response frequencies of the portion of the human body excited by the acoustic energy and analyzing the detected signal at the end of the defined time width; and
   e. comparing the response frequencies of the detected signals to predetermine known frequencies to determine information about the physical and structural characteristics of the portion of the human body.

2. The non-invasive method in accordance with claim 1, further comprising: said detected signals are used to identify diseases of the portion of the human body.

3. The non-invasive method in accordance with claim 2, further comprising: the disease identified further comprises a disease of a static body portion selected from the group consisting of bones, tissue implants, mechanical implants, breast tissue, calcified tissues, sclerotic lesions, the spine and organs.

4. The non-invasive method in accordance with claim 2, further comprising: the disease identified further comprises a disease of a dynamic body portion selected from the group consisting of arterial plaque, vulnerable plaque, damaged natural heart valves, malfunctioning natural heart valves, damaged mechanical heart valves, malfunctioning bioprosthetic heart valves, muscle infractions and lungs.

5. The non-invasive method in accordance with claim 1, further comprising: the first point in time is delayed by 80 ms relative to the time of origin, the second point in time is 160 ms relative to the time of origin, the third point in time is delayed by 240 ms relative to the time of origin, and the time widths of the respective first, second and third fixed frequencies are identical and range from 1 to 15 ms.

6. The non-invasive method in accordance with claim 1, further comprising: the first fixed frequency, the second fixed frequency and the third fixed frequency are identical and have a range of 1 to 20 MHz, the first center frequency is 2.2 KHz with the first bandwidth of 200 Hz, the second center frequency is 4.4 KHz with the second bandwidth of 1,000 Hz, and the third center frequency is 7.4 KHz with the third bandwidth of 1,200 Hz.

7. The non-invasive method in accordance with claim 6, further comprising: each individual presentation respectively containing a given one of the three chirps is broken down into different segments so that swept frequencies occur in a sequence that is specific and controllable so that the chirps cover the frequency range of 1 to 20 MHz and search for any resonance or signature response frequencies of the portion of the human body.

8. The non-invasive method in accordance with claim 1, further comprising: performing the non-invasive method while other contaminating noises are minimal or have been reduced to a minimum, so that each individual presentation respectively containing a given one of the three chirps is broken down into different segments so that the swept frequencies occur in a sequence that is particular and controllable in order to maximize the time for which each frequency sweeping is introduced, which in turn increases the signal-to-noise ratio (S/N).

9. The non-invasive method in accordance with claim 1, further comprising:
   a. using a DAQ box to generate the respective digital pulses, wherein operation of the DAQ box is controlled by a chirp generation program installed in a computer;
   b. using the computer to control operation of the non-invasive method;
   c. amplifying the respective fixed frequencies by a first power amplifier prior to frequencies being applied to the ultrasonic transducer, amplifying the respective modulated frequencies by a second power amplifier prior to the frequencies being applied to the ultrasonic transducer;
   d. using at least one detector selected from the group consisting of a microphone and a hydrophone to detect the signal that is a stimulated acoustic vibration from the portion of the human body; and
   e. applying amplification and filtering of the signal obtained from the at least one detector prior to analyzing the signal.

10. The non-invasive method in accordance with claim 9, wherein the ultrasonic transducer is selected from the group consisting of a single-element focused transducer and a single-element unfocused transducer, and is connected to a combiner that is connected to the first and second function generators.

11. The non-invasive method in accordance with claim 9, wherein the ultrasonic transducer is selected from the group consisting of a dual-element confocal transducer and a focused transducer.

12. The non-invasive method in accordance with claim 9, further comprising: a trigger which is an "R" wave of a "QRS" Complex.

13. The non-invasive method in accordance with claim 9, further comprising: using an oscilloscope to visualize inputs to the transducer, the signal from the at least one detector, and the respective fixed and modulated frequencies.

14. The non-invasive method in accordance with claim 9, further comprising: the ultrasonic transducer is selected from the group consisting of a non-imaging mechanical ultrasonic transducer, non-imaging electronic ultrasonic transducer, imaging mechanical ultrasonic transducer and an imaging electronic ultrasonic transducer.

15. The non-invasive method in accordance with claim 14, further comprising: the ultrasonic imaging transducer is selected from the group consisting of a linear transducer and a linear-array transducer.

16. The non-invasive method in accordance with claim 14, further comprising: the ultrasonic imaging transducer is a phased-array electronic transducer.

17. The non-invasive method in accordance with claim 9, further comprising: the ultrasonic imaging transducer is a single element transducer connected to a combiner which is connected to the first and second function generators.

18. The non-invasive method in accordance with claim 9, further comprising: the ultrasonic transducer is a non-imaging transducer.

19. The non-invasive method in accordance with claim 18, further comprising: the non-imaging transducer is selected from the group consisting of single-element, multi-element, focused and unfocused transducers.

20. The non-invasive method in accordance with claim 18, further comprising: the non-imaging transducer is cylindrical.

21. The non-invasive method in accordance with claim 1, further comprising: filtering means including a forced window which is open for a short period of time during analysis and an exponential window which is used to obtain responses from the excited portion of the human body.

22. The non-invasive method in accordance with claim 1, further comprising: the at least one detector is comprised of a group consisting of a microphone, microphones, a hydrophone and hydrophones, and each microphone and hydrophone having a receiving sensitivity.

23. The non-invasive method in accordance with claim 22, further comprising: the at least one detector is selected from the group consisting of an accelerometer and laser vibrometer, used for investigation and validation of the detected signal.

24. A non-invasive method to identify the physical characteristics of a portion of a human body, comprising:
   a simultaneously triggering first and second function generators at a first time to thereby transmit a respective first fixed frequency and first chirp that are sent to an ultrasonic transducer which generates an acoustic energy or radiation force to input and excite the portion of the human body, detecting a signal of response frequencies of the portion of the human body and analyzing the detected signal;
   b. simultaneously triggering the first and second function generators at a second time to thereby transmit a respective second fixed frequency and a second chirp that are sent to the ultrasonic transducer which generates an acoustic energy or radiation force to impact and excite the portion of the human body, detecting a signal of response frequencies of the portion of the human body and analyzing the detected signal;

c. simultaneously triggering first and second function generators at a third time to thereby transmit a respective third fixed frequency and third chirp that are sent to the ultrasonic transducer which generates an acoustic energy or radiation force to impact and excite the portion of the human body, detecting a signal of response frequencies of the portion of the human body and analyzing the detected signal;

d. applying a trigger that generates a first pulse to trigger the first and second function generators at a first time according to a first point in time relative to a time of origin, wherein the first fixed frequency has a defined time width, and the first chirp is a signal of modulated frequencies created from modulating a fixed frequency equivalent to the first fixed frequency having the defined time width and swept frequencies having a first center frequency with a first bandwidth;

e. applying a trigger that generates a second pulse to trigger the first and second function generators at a second time according to a second point in time relative to the time of origin, wherein the second fixed frequency has a defined time width, and the second chirp is a signal of modulated frequencies created from modulating a fixed frequency equivalent to the second fixed frequency having the defined time width and swept frequencies having a second center frequency with a second bandwidth;

f. applying a trigger that generates a third pulse to trigger the first and second function generators at a third time according to a third point in time relative to the time of origin, wherein the third fixed frequency has a defined time width, and the third chirp is a signal of modulated frequencies created from modulating a fixed frequency equivalent to the third fixed frequency having the defined time width and swept frequencies having a third center frequency with a third bandwidth; and g. comparing responsive frequencies of the detected signals to predetermined known frequencies to determine information about the physical and structural characteristics of the portion of the human body.

25. The non-invasive method in accordance with claim 24, further comprising: said detected signals are used to identify diseases of the portion of the human body.

26. The non-invasive method in accordance with claim 25, further comprising: the disease identified further comprises a disease of a static body portion selected from the group consisting of bones, tissue implants, mechanical implants, breast tissue, calcified tissues, sclerotic lesions, the spine and organs.

27. The non-invasive method in accordance with claim 25, further comprising: the disease identified further comprises a disease of a dynamic body portion selected from the group consisting of arterial plaque, vulnerable plaque, damaged natural heart valves, malfunctioning natural heart valves, damaged mechanical heart valves, malfunctioning bioprosthetic heart valves, muscle infractions and lungs.

28. The non-invasive method in accordance with claim 24, further comprising: the first point in time is delayed by 80 ms relative to the time of origin, the second point in time is 160 ms relative to the time of origin, the third point in time is delayed by 240 ms relative to the time of origin, and the time widths of the respective first, second and third fixed frequencies are identical and range from 1 to 15 ms.

29. The non-invasive method in accordance with claim 24, further comprising: the first fixed frequency, the second fixed frequency and the third fixed frequency are identical and have a range of 1 to 20 MHz, the first center frequency is 2.2 KHz with the first bandwidth of 200 Hz, the second center frequency is 4.4 KHz with the second bandwidth of 1,000 Hz, and the third center frequency is 7.4 KHz with the third bandwidth of 1,200 Hz.

30. The non-invasive method in accordance with claim 29, further comprising: each individual presentation respectively containing a given one of the three chirps is broken down into different segments so that swept frequencies occur in a sequence that is specific and controllable so that the chirps cover the frequency range of 1 to 20 MHz and search for any resonance or signature response frequencies of the portion of the human body.

31. The non-invasive method in accordance with claim 24, further comprising: performing the non-invasive method while other contaminating noises are minimal or have been reduced to a minimum, so that each individual presentation respectively containing a given one of the three chirps is broken down into different segments so that the frequencies occur in a sequence that is particular and controllable in order to maximize the time for which each frequency sweeping is introduced, which in turn increases the signal-to-noise ratio (S/N).

32. The non-invasive method in accordance with claim 24, further comprising:

a. using a DAQ box to generate the respective digital pulses, wherein operation of the DAQ box is controlled by a chirp generation program installed in a computer;

b. using the computer to control operation of the non-invasive method;

c. amplifying the respective fixed frequencies by a first power amplifier prior to frequencies being applied to the ultrasonic transducer, amplifying the respective modulated frequencies by a second power amplifier prior to the frequencies being applied to the ultrasonic transducer;

d. using the at least one detector selected from the group consisting of a microphone and a hydrophone to detect the signal that is a stimulated acoustic vibration from the portion of the human body; and e. amplifying and filtering the signal obtained from the at least one detector prior to analyzing the signal.

33. The non-invasive method in accordance with claim 32, wherein the ultrasonic transducer is selected from the group consisting of a single-element transducer, a linear transducer, a linear array transducer, a non-magnetic transducer, a single-element focused transducer, a single-element unfocused transducer, a multi-element focused transducer and a multi-element unfocused transducer, and is connected to a combiner that is connected to the first and second function generators.

34. The non-invasive method in accordance with claim 32, wherein the ultrasonic transducer is selected from the group consisting of a dual-element confocal transducer and a focused transducer.

35. The non-invasive method in accordance with claim 32, further comprising: a trigger which is an "R" wave of a "QRS" Complex".

36. The non-invasive method in accordance with claim 32, further comprising: using an oscilloscope to visualize inputs to the transducer, the signal from the at least one detector, and the respective fixed and modulated frequencies.

37. The non-invasive method in accordance with claim 32, further comprising: the ultrasonic transducer is selected from the group consisting of a non-imaging mechanical ultrasonic transducer, non-imaging electronic ultrasonic transducer, imaging mechanical ultrasonic transducer and an imaging electronic ultrasonic transducer.

38. The non-invasive method in accordance with claim 32, further comprising: the detector is comprised of a group consisting of a microphone, microphones, a hydrophone and hydrophones, and each microphone and hydrophone having a receiving sensitivity.

39. The non-invasive method in a accordance with claim 24, further comprising filtering means including a forced window which is open for a short period of time during analysis and an exponential window which is used to obtain sharp responses from the excited body part.

40. The non-invasive method in accordance with claim 39, further comprising: the detector is selected from the group consisting of an accelerometer and laser vibrometer, used for investigation and validation of the detected signal.

41. A non-invasive method to identify physical characteristics of a target in a human body, comprising:
 a. setting a time of origin in a time scheme of the non-invasive method;
 b. generating a first fixed frequency and a first chirp at a first point in time of the time scheme, to simultaneously trigger first and second function generators of the first generator, the first function generator generating a first fixed frequency to an ultrasonic transducer having a defined time width, the second function generator transmitting a first chirp of modulating frequencies to an ultrasonic transducer having the defined time width, the ultrasonic transducer generating an oscillating acoustic force to input and excite the portion of the human body using at least one detector to detect a signal of response frequencies from and as the result of the portion of the human body excited by the acoustic force and analyzing the detected signal at an end of the defined time width;
 c. generating a second fixed frequency and a second chirp to simultaneously trigger first and second function generators, the first function generator generating a second fixed frequency, an ultrasonic transducer having a defined time width, the second function generator transmitting a second chirp of modulated frequencies, the ultrasonic transducer having the defined time width, the ultrasonic transducer generating an oscillating acoustic force to input and excite the portion of the human body, using at least one detector to detect the signal of response frequencies from and as the result of the portion of the human body excited by the acoustic energy or radiation force and analyzing the detected signal at an end of the defined time width;
 d. generating a third fixed frequency and a third chirp to simultaneously trigger first and second function generators, the first function generator generating a third fixed frequency, the ultrasonic transducer having a defined time width, the second function generator transmitting a third chirp of modulated frequencies to the ultrasonic transducer having the defined time width, the ultrasonic transducer generating an oscillating acoustic force to input and excite the portion of the human body using at least one detector to detect a signal of response frequencies from and as the result of the portion of the human body excited by the acoustic energy or radiation force and analyzing the detected signal at an end of the defined time width; and
 e. applying the first fixed frequency and first chirp, the second fixed frequency and second chirp, and the third fixed frequency and third chirp to identify the physical characteristics of the target in the human body.

42. The non-invasive method in accordance with claim 41 further comprising: incorporating a first function generator, a second function generator, a trigger, an ultrasonic transducer and at least one detector into the non-invasive method.

43. The non-invasive method in accordance with claim 42, further comprising: the first fixed frequency, the second fixed frequency and the third fixed frequency are identical and have a range of 1 to 20 MHz, the first center frequency is 2.2 KHz with the first bandwidth of 200 Hz, the second center frequency is 4.4 KHz with the second bandwidth of 1,000 Hz, and the third center frequency is 7.4 KHz with the third bandwidth of 1,200 Hz.

44. The non-invasive method in accordance with claim 43, further comprising: each individual presentation respectively containing a given one of the three chirps is broken down into different segments so that swept frequencies occur in a sequence that is specific and controllable so that the chirps cover the desired frequency ranges of 1-20 MHz and search for any resonance or signature response frequencies of the portion of human body.

45. A non-invasive method to identify the physical characteristics of a portion of a human body, comprising:
 a. setting a time of origin in a time scheme of the non-invasive method;
 b. generating a first pulse from the trigger at a first point in time of the time scheme, which first pulse is sent to simultaneously trigger first and second function generators, the first function generator generating a first fixed frequency to an ultrasonic transducer having a defined time width, the second function generator transmitting a first chirp of a modulated frequency to the ultrasonic transducer having the defined time width, the ultrasonic transducer generating an acoustic energy or radiation force to input and excite the portion of the human body using at least one detector to detect a signal of response frequencies from and as a result of the portion of the human body excited by the acoustic energy or radiation force and analyzing the detected signal at an end of the defined time width;
 c. generating a second pulse from the trigger at a second point in time of the time scheme, which second pulse is sent to simultaneously trigger the first and second function generators, the first function generator generating a first fixed frequency having a defined time width to an ultrasonic transducer, the second function generator transmitting a first chirp of a modulated frequency having the defined time width to the ultrasonic transducer, the ultrasonic transducer generating an oscillating acoustic force to input and excite the portion of the human body using at least one detector to detect a signal of response frequencies from and as the result of the portion of the human body excited by the acoustic energy or radiation force and analyzing the detected signal at an end of the defined time width; and
 d. generating a third pulse from the trigger at a third point in time of the time scheme, which third pulse is sent to simultaneously trigger first and second function generators, the first function generator generating a first frequency to an ultrasonic transducer having a defined time width, the second function generator transmitting a first chirp of the modulated frequencies to the ultrasonic transducer having the defined time width, the ultrasonic transducer generating an acoustic energy or radiation force to input and excite the portion of the human body using at least one detector to detect a signal of response frequencies from the portion of the human body excited by the acoustic energy or radiation force and analyzing the detected signal at an end of the defined time width.

46. A non-invasive method in accordance with claim 45, further comprising:
   a. the first chirp of modulated frequencies are created from modulating a fixed frequency equivalent to the first fixed frequency and swept frequencies having a first bandwidth and the defined time width;
   b. the modulated frequencies from the second chirp are created from modulating a fixed frequency equivalent to the second fixed frequency and swept frequencies having a center frequency with a second bandwidth and the defined time width;
   c. the modulated frequency generated from the third chirp are created from modulating a fixed frequency equivalent to the third frequency and swept frequencies having a third center frequency with a third bandwidth and the defined time width; and
   d. comparing the response frequencies of the detected signals, the predetermined known frequencies to determine information about the physical and structural characteristics of the portion of the human body.

47. The non-invasive method in accordance with claim 45, further comprising said detected signals are used to identify diseases of the portion of the human body.

48. The non-invasive method in accordance with claim 47, further comprising the diseases identified further comprise the disease of a static portion selected from the group consisting of bones, tissue implants, mechanical implants, breast tissue, calcification tissues, sclerotic lesions, the spine and organs.

49. The non-invasive method in accordance with claim 47, further comprising: the disease identified further comprises a disease of a dynamic body portion selected from the group consisting of arterial plaque, vulnerable plaque, damaged natural heart valves, malfunctioning natural heart valves, damaged mechanical heart valves, malfunctioning biprosthetic heart valves, muscle infractions and lungs.

50. The non-invasive method in accordance with claim 45, further comprising: the first point in time is delayed by up to 80 ms relative to the time of origin, the second point in time is delayed by up to 60 ms relative to the time of origin, the third point in time is delayed by up to 240 ms relative to the time of origin, and the time widths of the respective first, second and third fixed frequencies are identical and range from 1 to 15 ms.

51. The non-invasive method in accordance with claim 45, further comprising: performing the non-invasive method by choice in a noise-free environment so that each individual presentation respectively containing a given one of the three chirps is broken down into different segments so that the swept frequencies occur in a sequence that is particular and controllable in order to maximize the time for which each frequency sweeping is introduced, which in turn increases the signal-to-noise ratio (S/N).

52. The non-invasive method in accordance with claim 45, further comprising:
   a. using a DAQ box to generate the respective digital pulses, wherein operation of the DAQ box is controlled by a trip generator program installed in a computer;
   b. using the computer to control operation of the non-invasive method;
   c. amplifying the respective fixed frequencies by a first power amplifier prior to frequencies being applied to the ultrasonic transducer, amplifying the respective modulated frequencies by a second power amplifier prior to the frequencies being applied to the ultrasonic transducer;
   d. using at least one detector selected from the group consisting of a microphone and a hydrophone to detect the signal that is a stimulated acoustic vibration from the portion of the human body; and
   e. applying amplification and filtering of the signal obtained from the at least one detector prior to analyzing the signal.

53. The non-invasive method in accordance with claim 52, wherein the ultrasonic transducer is selected from the group consisting of a single-element focused transducer and a single-element unfocused transducer, and is connected to a combiner that is connected to the first and second function generators.

54. The non-invasive method in accordance with claim 52, wherein the ultrasonic transducer is selected from the group consisting of a dual-element confocal transducer and a focused transducer.

55. The non-invasive method in accordance with claim 52, further comprising: the trigger is an "R wave" of a "QRS" Complex.

56. The non-invasive method in accordance with claim 52, further comprising: using an oscilloscope to visualize inputs to the transducer, the signal from the at least one detector, and the respective fixed and modulated frequencies.

57. The non-invasive method in accordance with claim 52, further comprising: the ultrasonic transducer is selected from the group consisting of a non-imaging mechanical ultrasonic transducer, non-imaging electronic ultrasonic transducer, imaging mechanical ultrasonic transducer and an imaging electronic ultrasonic transducer.

58. The non-invasive method in accordance with claim 52, further comprising: the ultrasonic imaging transducer is a single element transducer connected to a combiner which is connected to the first and second function generators.

59. The non-invasive method in accordance with claim 52, further comprising: the ultrasonic imaging transducer is selected from the group consisting of a linear transducer and a phased-array transducer.

* * * * *